US 8,361,453 B2

(12) United States Patent
Uhrich et al.

(10) Patent No.: US 8,361,453 B2
(45) Date of Patent: Jan. 29, 2013

(54) IODINATED POLYMERS

(75) Inventors: Kathryn E. Uhrich, Plainfield, NJ (US); Ashley Carbone, North Haledon, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 425 days.

(21) Appl. No.: 12/303,682

(22) PCT Filed: Jun. 6, 2007

(86) PCT No.: PCT/US2007/070531
§ 371 (c)(1),
(2), (4) Date: Sep. 1, 2010

(87) PCT Pub. No.: WO2007/143698
PCT Pub. Date: Dec. 13, 2007

(65) Prior Publication Data
US 2011/0022161 A1    Jan. 27, 2011

Related U.S. Application Data

(60) Provisional application No. 60/811,261, filed on Jun. 6, 2006.

(51) Int. Cl.
*A61K 31/74* (2006.01)
(52) U.S. Cl. .................. 424/78.08; 424/78.01
(58) Field of Classification Search ............. 424/78.01
See application file for complete search history.

(56) References Cited

U.S. PATENT DOCUMENTS

| | | | |
|---|---|---|---|
| 3,044,942 A | | 7/1962 | Noel |
| 3,371,070 A | * | 2/1968 | Chang et al. .................. 528/365 |
| 4,139,605 A | * | 2/1979 | Felder et al. ............... 424/9.452 |
| 4,757,128 A | | 7/1988 | Domb et al. |
| 4,789,724 A | | 12/1988 | Domb et al. |
| 4,832,940 A | * | 5/1989 | Ege ............................. 424/1.41 |
| 4,857,311 A | | 8/1989 | Domb et al. |
| 4,888,176 A | | 12/1989 | Langer et al. |
| 6,103,255 A | * | 8/2000 | Levene et al. ................. 424/426 |
| 6,238,687 B1 | * | 5/2001 | Mao et al. .................... 424/426 |
| 6,468,519 B1 | * | 10/2002 | Uhrich ........................ 424/78.01 |
| 6,475,477 B1 | * | 11/2002 | Kohn et al. ............... 424/78.08 |
| 6,486,214 B1 | | 11/2002 | Uhrich |
| 6,602,915 B2 | | 8/2003 | Uhrich |
| 6,613,807 B2 | | 9/2003 | Uhrich |

(Continued)

FOREIGN PATENT DOCUMENTS

| WO | WO 95/03357 | 2/1995 |
|---|---|---|
| WO | WO 99/12990 | 3/1999 |

(Continued)

OTHER PUBLICATIONS

Patent Cooperation Treaty, International Search Report and Written Opinion of PCT/US07/70531, 11 pages, dated Nov. 29, 2007.

(Continued)

*Primary Examiner* — James J Seidleck
*Assistant Examiner* — Peter A Salamon
(74) *Attorney, Agent, or Firm* — Viksnins Harris & Padys PLLP

(57) ABSTRACT

The invention provides medical devices that comprise an iodinated polymer and that can be viewed using X-Ray imaging techniques. The invention also provides novel iodinated polymers that can be incorporated into or coated on medical devices.

23 Claims, 1 Drawing Sheet

U.S. PATENT DOCUMENTS

| | | | | |
|---|---|---|---|---|
| 6,623,521 | B2* | 9/2003 | Steinke et al. | 623/1.16 |
| 6,626,936 | B2* | 9/2003 | Stinson | 623/1.15 |
| 6,685,928 | B2 | 2/2004 | Uhrich et al. | |
| 6,689,350 | B2 | 2/2004 | Uhrich | |
| 6,951,053 | B2* | 10/2005 | Padilla et al. | 29/557 |
| 7,122,615 | B1 | 10/2006 | Uhrich | |
| 7,396,527 | B2 | 7/2008 | Uhrich | |
| 7,411,031 | B2 | 8/2008 | Uhrich et al. | |
| 7,534,852 | B2 | 5/2009 | Uhrich | |
| 7,553,325 | B2* | 6/2009 | Stinson | 623/1.34 |
| 7,582,110 | B2* | 9/2009 | Case et al. | 623/1.24 |
| 7,637,937 | B2* | 12/2009 | Case et al. | 623/1.15 |
| 7,662,864 | B2 | 2/2010 | Kanamathareddy et al. | |
| 7,666,398 | B2 | 2/2010 | Uhrich | |
| 7,879,062 | B2* | 2/2011 | Galdonik et al. | 606/200 |
| 7,985,415 | B2 | 7/2011 | Giroux | |
| 8,017,714 | B2 | 9/2011 | Uhrich | |
| 8,088,405 | B2 | 1/2012 | Uhrich | |
| 2001/0021873 | A1* | 9/2001 | Stinson | 623/1.34 |
| 2001/0044651 | A1* | 11/2001 | Steinke et al. | 623/1.16 |
| 2001/0047185 | A1* | 11/2001 | Satz | 606/198 |
| 2003/0199969 | A1* | 10/2003 | Steinke et al. | 623/1.16 |
| 2004/0038948 | A1 | 2/2004 | Uhrich | |
| 2004/0096476 | A1 | 5/2004 | Uhrich et al. | |
| 2004/0111149 | A1* | 6/2004 | Stinson | 623/1.34 |
| 2004/0127971 | A1* | 7/2004 | Padilla et al. | 623/1.15 |
| 2005/0036946 | A1* | 2/2005 | Pathak et al. | 424/9.4 |
| 2005/0048121 | A1* | 3/2005 | East et al. | 424/486 |
| 2005/0085847 | A1* | 4/2005 | Galdonik et al. | 606/200 |
| 2005/0131199 | A1 | 6/2005 | Uhrich et al. | |
| 2005/0228472 | A1* | 10/2005 | Case et al. | 623/1.1 |
| 2005/0228486 | A1* | 10/2005 | Case et al. | 623/1.24 |
| 2005/0249697 | A1 | 11/2005 | Uhrich et al. | |
| 2006/0004440 | A1* | 1/2006 | Stinson | 623/1.34 |
| 2006/0013851 | A1 | 1/2006 | Giroux | |
| 2006/0020331 | A1* | 1/2006 | Bates et al. | 623/1.49 |
| 2006/0034769 | A1 | 2/2006 | Kohn et al. | |
| 2006/0036316 | A1* | 2/2006 | Zeltinger et al. | 623/1.49 |
| 2006/0057179 | A1 | 3/2006 | Giroux | |
| 2007/0098800 | A1 | 5/2007 | Giroux et al. | |
| 2007/0196417 | A1 | 8/2007 | Uhrich | |
| 2008/0226583 | A1 | 9/2008 | Uhrich | |
| 2008/0233078 | A1 | 9/2008 | Uhrich | |
| 2009/0035248 | A1 | 2/2009 | Uhrich et al. | |
| 2010/0152410 | A1 | 6/2010 | East et al. | |
| 2010/0272670 | A1 | 10/2010 | Uhrich et al. | |
| 2010/0291180 | A1 | 11/2010 | Uhrich | |
| 2010/0291181 | A1 | 11/2010 | Uhrich et al. | |
| 2010/0310498 | A1 | 12/2010 | Kanamathareddy et al. | |
| 2012/0058155 | A1 | 3/2012 | Uhrich et al. | |

FOREIGN PATENT DOCUMENTS

| | | | |
|---|---|---|---|
| WO | WO 9912990 A1 * | 3/1999 | |
| WO | WO 01/28492 | 4/2001 | |
| WO | WO 01/41753 | 6/2001 | |
| WO | WO 02/09767 | 2/2002 | |
| WO | WO 02/09768 | 2/2002 | |
| WO | WO 02/09769 | 2/2002 | |
| WO | WO 03/046034 | 6/2003 | |
| WO | WO 03/065928 | 8/2003 | |
| WO | WO 03/066053 | 8/2003 | |
| WO | WO 03/072020 | 9/2003 | |
| WO | WO 2004/006863 | 1/2004 | |
| WO | WO 2004/039355 | 5/2004 | |
| WO | WO 2004/045549 | 6/2004 | |
| WO | WO 2005/039489 | 5/2005 | |
| WO | WO 2005/042600 | 5/2005 | |
| WO | WO 2006020616 A1 * | 2/2006 | |
| WO | WO 2006/127667 | 11/2006 | |
| WO | WO 2008/034019 | 3/2008 | |
| WO | WO 2008/103744 | 8/2008 | |
| WO | WO 2008/128193 | 10/2008 | |
| WO | WO 2009/026544 | 2/2009 | |

OTHER PUBLICATIONS

Davy et al., "X-Ray Opaque Methacrylate Polymers for Biomedical Applications", *Polymer International*, 43(2), 143-154 (1997).

Lin et al., "Antimicrobial activities of iodinated polystyrene derivatives", *Artificial Organs*, 20(11), 1191-1195 (1996).

Kruft et al., "Studies on radio-opaque polymeric biomaterials with potential applications to endovascular prostheses", *Biomaterial*, 17(18), 1803-1812 (1996).

Kruft et al., "In vivo tissue compatibility of two radio-opaque polymeric biomaterials", *Biomaterials*, 18(1), 31-36 (1997).

* cited by examiner

IODINATED POLYMERS

RELATED APPLICATION

This application is a National Stage application under 35 U.S.C. §371 of International Application No. PCT/US2007/070531 having an International Filing Date of Jun. 6, 2007 and claims the benefit of priority of U.S. application Ser. No. 60/811,261, filed Jun. 06, 2006, which applications are incorporated herein by reference in their entireties.

STATEMENT OF GOVERNMENT SUPPORT

This invention was made with government support under grant number DE 13207 awarded by the National Institutes of Health. The government has certain rights in the invention.

BACKGROUND OF THE INVENTION

International Patent Applications WO 1999/012990, WO 2002/009768, and WO 2002/009767, as well as U.S. Pat. Nos. 6,486,214, 6,613,807, and 6,689,350, discuss biodegradable polymers that have a therapeutic agent incorporated into the polymer backbone. The polymers are reported to be useful materials for forming or for coating medical articles (e.g. devices such as stents), as they degrade and thereby deliver the therapeutic agent to a host.

One potential difficulty encountered with articles formed from such polymeric materials is that, unlike metal articles, the polymeric articles are not visible using X-Ray imaging techniques. Thus, it is not possible to monitor the placement of the polymeric articles during or after implantation into a subject. This limits the practical uses of polymeric articles prepared from these and other polymeric materials.

Accordingly, there is currently a need for materials that can be used to prepare polymeric articles that are visible using X-Ray imaging techniques.

SUMMARY OF THE INVENTION

The present invention provides iodinated polymers that can be used to form or coat articles to provide articles that are visible using X-Ray imaging techniques. Accordingly, one embodiment of the invention provides an article (e.g. an implantable medical device) comprising a biodegradable, iodinated polymer (e.g., an article coated with the biodegradable, iodinated polymer). Other applications in which the X-Ray visible polymer materials (e.g., articles, e.g. articles coated with the polymer) may be useful include veterinary medicine; security or identifying taggants for food, cosmetic, pharmaceutical, chemical, agricultural or vetinary products; industries to coat products, equipment or parts to ensure they do not have flaws or cracks; archaeological applications for the nondestructive investigation of fossils; or security applications to detect dangerous substances.

In another embodiment, the invention provides novel biodegradable iodinated polymers (e.g. a polyanhydride, polyester, polycarbonate or polyamide) having a backbone comprising one or more iodinated aryl rings.

The invention also provides processes and intermediated disclosed herein that are useful for preparing iodinated polymers and articles that comprise iodinated polymers.

The mechanical and thermal properties of the iodinated polymers may allow articles to be prepared from the polymers as well as being coated with the iodinated polymers.

DETAILED DESCRIPTION

Figure 1:
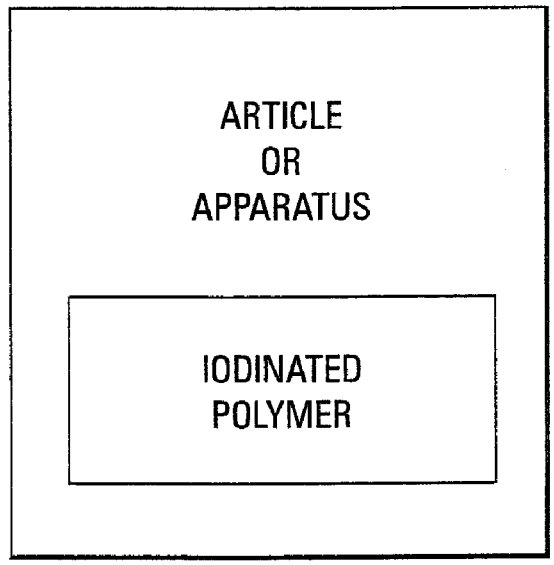
FIG. 1 is a block diagram of an apparatus or article including an iodinated polymer in accordance with some embodiments.

X-ray opaque iodinated salicylic acid-based poly(anhydride-esters) were synthesized using two different methods, melt-condensation and solution polymerization. The different polymerization methods yielded polymers with different properties, X-ray visibility and cell biocompatibility. In general, polymers prepared by melt-condensation methods (4a-c) resulted in materials with higher glass transition temperatures and higher Young's modulus than the corresponding polymers made via low-temperature solution polymerization (5a-c). Polymers made via melt-condensation (4a-c) were also found to have larger molecular weights, broader polydispersity indices and higher X-ray opacity. The choice of synthetic procedure will likely depend on the final application and desired properties. For example, when preparing copolymers or admixtures of these radiopaque polymers with heat sensitive drugs, solution polymerization will most likely be the method of choice.

Cytocompatibility of iodinated salicylic acid-based polymers was first evaluated by exposing L929 fibroblast cells in media containing polymers for 3 days. Compared to the controls, cells showed positive growth cycles with normal stellate morphology of fibroblasts at the lower concentration (0.01 mg/mL) of polymer, except with polymer 5b for 3 days. At higher polymer concentration (0.1 mg/mL), cellular morphology and proliferation in media containing 5-iodosalicylic acid-based-polymers (4a, 5a) did not show difference from the control, whereas, cells in presence of 3,5-diiodosalicylic acid-based-polymers (4b, 5b) exhibited less compatibility. In the second series of studies, cells were cultured on polymer-coated glass surfaces, and cell morphology and numbers studied. L929 mouse fibroblasts attached and proliferated on day 1, but did not show normal growth cycles on day 2 and 3. Cellular responses on the 5-iodosalicylic acid-based polymers were the same for both melt-condensation (4a, 4b) and solution (5a, 5b) polymerization methods, with the only difference between 4c and 5c. From the degradation of the polymer-coated coverslips, a significantly high local concentration of free drug (1a-c) in the cell media may have negatively affected cell attachment and proliferation. Overall, the iodinated salicylic acid-based poly(anhydride-esters) had favorable cell biocompatibility at low concentrations, indicating the possibility of using these radiopaque polymer systems as or in conjunction with biomaterials.

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or a bicyclic carbocyclic radical (e.g., an ortho-fused bicyclic carbocyclic radical) having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of a bicyclic heterocycle (e.g., an ortho-fused bicyclic heterocycle) of about eight to ten ring atoms derived therefrom, particularly a benz-derivative or one derived by fusing a propylene, trimethylene, or tetramethylene diradical thereto.

Specific and preferred values listed below for radicals, substituents, and ranges, are for illustration only; they do not exclude other defined values or other values within defined ranges for the radicals and substituents.

Specifically, ($C_1$-$C_6$) alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

It is common to view implantable metal devices with X-rays during or following implantation to determine the location of the device. Unfortunately, it is not possible to view many non-metallic devices using X-rays. The invention provides articles that comprise X-ray opaque iodo groups. The iodo groups can be incorporated into the material of which the article is made, or the iodo-groups can be present in a material that is coated on the article.

Implantable Devices

In one embodiment the invention provides implantable medical devices that are visible using X-ray imaging technology. The devices can be made of any suitable material including metal, metal alloys, ceramics, glass, inorganic polymers, and organic polymers. For example, the implantable medical devices can include a stent, an orthopedic device, a bone plate, a pacemaker, a pump, a screw, a pin, a catheter, a graft, a suture, a surgical mesh, a microsphere, a film, a fiber, an intraocular lense, a surgical laser, a defibrillator, a lead or electrode for a pacemaker or defibrillator, an infusion pump, a hearing aid, a ventilator, an implantable drug pump, a cosmetic implant such as a breast or calf implant, a colonoscope, a gastroscope, an endotracheal tube, a bronchoscope, a dental prostheses, an orthodontic device, an intrauterine device, an oxygenator, a replacement joint, a bone prostheses, a cement, a replacement tendon, an artificial larynx, a ligation clip, and a ventricular-assist device.

In some embodiments of the invention, the iodo-groups are present in the backbone of a polymer, e.g., to form an iodinated polymer.

In one embodiment of the invention, the device can be made from a material that comprises iodo-groups (e.g. aryl iodo-groups) (e.g., the device is formed from material admixed with an iodinated polymer). For example, the device can be made from a polymer or a copolymer that has aromatic or aliphatic iodine groups in the polymer backbone (e.g., aryl-iodo groups in the polymer backbone).

In another embodiment of the invention, the device is made from a metal, glass, or polymer and is coated with a material that comprises iodo-groups (e.g. aryl iodo-groups). In another embodiment of the invention, the device is made from a metal, glass, or polymer and is coated with a material that comprises an iodinated polymer. The coating can comprise an iodinated polymer. Typically, the polymer coating is from about 1 mm to about 50 mm thick (e.g., about 1, 2, 5, 10, 25, 50, 1-10, 1-20, or 1-25 mm thick). In one specific embodiment of the invention, the polymer coating is from about 5 mm to about 25 mm thick. In one embodiment of the invention, the polymer coating is less than about 1 mm thick. The invention also provides articles that are made from a material that comprises iodo-groups and that further comprise a coating that comprises iodo-groups.

Materials

The articles of the invention can be made from any suitable material including metal, metal alloys, glass, ceramics, inorganic polymers, and organic polymers. In some embodiments of the invention, the iodinated polymer is admixed with a suitable material to make the article. One of skill in the art can readily select an appropriate polymeric material with sufficient mechanical stability and properties to be used for a selected application. Examples of polymers that may be useful include polyacrylates, polymethylacrylates, polycarbonates, polystyrenes, polysulphones, poly(hydroxy acids), polyanhydrides, polyorthoesters, polyphosphazenes, polyphosphates, polyesters, nylons or mixtures thereof. Examples of polymers of poly(hydroxy acids) include poly(hydroxybutyric acid), poly(lactic acid), poly(glycolic acid) and poly (caproic acid). Polyanhydrides, polyorthoesters, polyphosphazenes, polyphosphates, polycaprolactone or copolymers prepared from the monomers of these polymers (see for example WO 95/03357) may also be used. Poly(ortho-esters), polyol/diketene acetals and related polymers are provided by Heller, ACS Symposium Series 567, 292-305, 1994. Examples of biodegradable hydrophobic polyanhydrides are disclosed, for example, in U.S. Pat. Nos. 4,757,128; 4,857, 311; 4,888,176 and 4,789,724. Polyhydroxybutyrates are disclosed in U.S. Pat. No. 3,044,942.

Polymers of lactic acid or glycolic acid, or copolymers of these monomers are contemplated, such as poly(lactic acid), poly(glycolic acid) or poly(lactic-co glycolic) acid, poly(E-caprolactone), poly(3-hydroxybutyrate), poly(p-dioxanone), poly(alkylene glycol), poly(ethylene fumarte) and poly(propylene fumarate).

Polyanhydrides for use in articles of the present invention include, but are not limited to: poly(sebacic anhydride), poly (carboxybiscarboxyphenoxy-hexane), poly[bis(p-carboxyphenoxy)methane], and copolymers thereof which are described by Tamada and Langer in Journal of Biomaterials Science Polymer Edition, 3:315 (1992) and by Domb in Chapter 8 of the Handbook of Biodegradable Polymers, ed. Domb A. J. and Wiseman R. M., Harwood Academic Publishers. Also contemplated are poly(amino acids), and poly (pseudo amino acids) that include those described by James and Kohn in pages 389-403 of Controlled Drug Delivery Challenges and Strategies, American Chemical Society, Washington D.C. Polyphosphazenes for use in the present invention include derivatives of poly[(dichloro)phosphazene] poly[(organo) phosphazenes] polymers described by Schacht in Biotechnology and Bioengineering, 52, 102-108, 1996.

In one specific embodiment, polyesters of poly(lactic-co-glycolic)acid ("PLGA") are used. These polymers are approved for parenteral administration by the FDA. Because PLGA degrades via non-enzymatic hydrolysis in the initial stages, in vivo degradation rates can be predicted from in vitro data. PLGA is also a desirable material because it degrades to lactic and glycolic acids, substances found naturally in the body.

Additionally, copolymers with amino acids can be used. For example, glycolic acid and glycine, or lactic acid and lysine as described in Barrera et al., J. Am. Chem. Soc., 115:11010 (1993) and Cook et al., J. Biomed. Mat. Res., 35:513 (1997). Biodegradable materials also include collagen and polysaccharide gels, for example, of hyaluronic acid. Copolymers of collagen and proteoglycans may also be used.

Protein polymers may also be used and are prepared by available protein chemistry and molecular biology techniques. For example, polymers based on silk or elastin repeating units may be prepared and are suitable for use in the present invention (Hubbell J A., Biotechnology, 13:565 (1995)).

It will be appreciated that some biocompatible polymers, for example, some natural polymers as described above, may degrade in response to cellular and enzymatic activity and that the rate of such degradation may vary depending on the environment or cultural conditions involved. The rate of degradation in a specific environment can be observed by methods known to one of skill in the art. For example, the rate of degradation can be observed by placing the polymeric article in the environment in which it will be used and observed how long it remains intact. Hence, degradation can readily be observed and manipulated by one of skill in the art. In addition, natural polymers, such as collagen can be incorporated into devices of the invention.

In one specific embodiment of the invention, the article is made of a biodegradable polymer (e.g. a polymer that hydrolytically degrades (or hydrolyzes) into smaller molecular weight components).

In one specific embodiment of the invention the biodegradable polymer is a polyanhydride comprised of units of formula (IX):

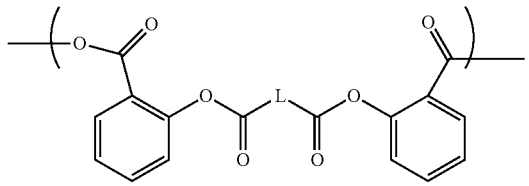

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—; each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In one embodiment of the invention L is a divalent, branched or unbranched, saturated or unsaturated, hydrocarbon chain, having 1, 2, 3, 4, 5, 6, 7, 8, 9, or 10 carbon atoms. In one specific embodiment of the invention, L is a divalent, unbranched, saturated hydrocarbon chain, having 8 carbon atoms. Methods for preparing such polyanhydrides are described in International Patent Application Number PCT/US01/23740.

Iodinated Polymers

The articles of the invention can be made from a material that comprises iodo-groups (e.g., admixed) and/or they can be coated with a material that comprises iodo-groups (e.g. an iodinated polymer). Suitable materials that comprise iodo-groups include iodinated polyanhydrides, iodinated polyesters, iodinated polycarbonates, and iodinated polyamides. In one embodiment of the invention, the iodinated polymer comprises iodinated aryl rings. In another embodiment of the invention, the iodinated groups are a component of the "L" linking groups.

In one specific embodiment of the invention, the iodinated polymer is an iodinated polyanhydride having a backbone that comprises one or more of the following residues:

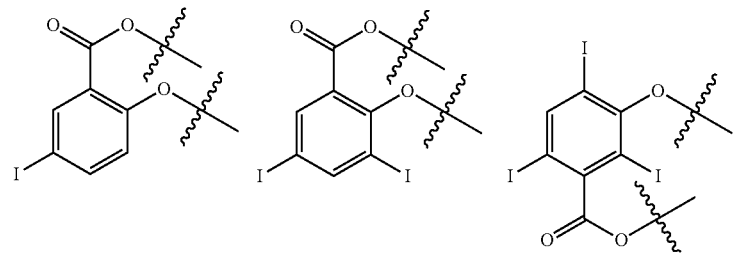

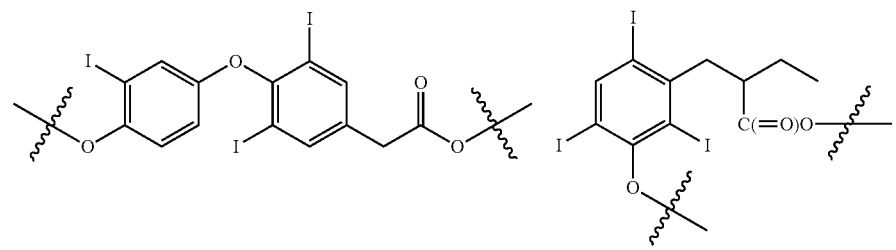

-continued

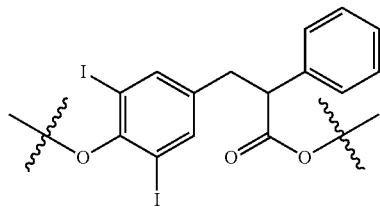

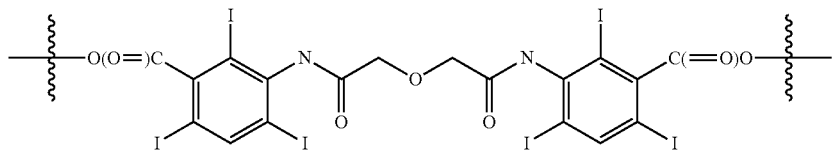

In another specific embodiment of the invention, the iodinated polymer comprises a residue of one or more of the following amino acids:

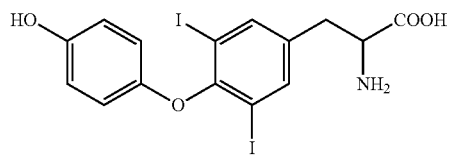

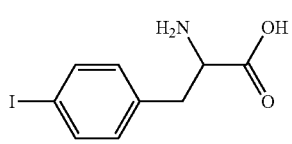

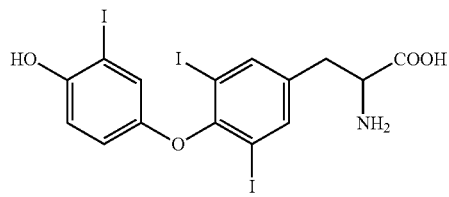

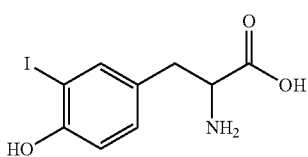

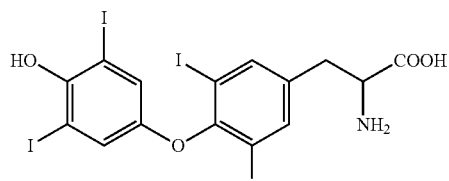

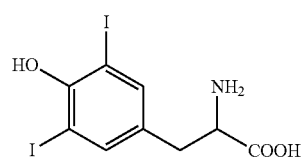

In another specific embodiment of the invention, the iodinated polymer is an iodinated polyanhydride that comprises repeating units of the following formula (I):

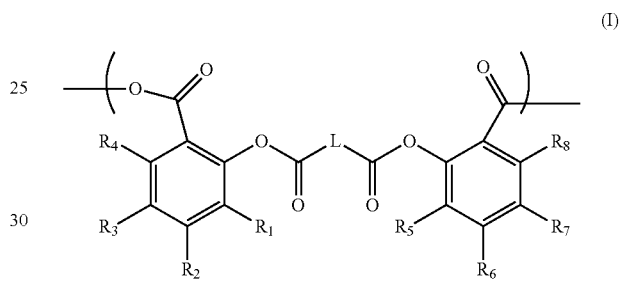

(I)

wherein:
at least one $R_1$, $R_2$, $R_3$, $R_4$, $R_5$, $R_6$, $R_7$, and $R_8$, is iodo and the rest of $R_1$, $R_2$, $R_3$, $R_4$, $R_5$, $R_6$, $R_7$, and $R_8$, are independently H or iodo; and L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;
each R is independently H or $(C_1-C_6)$alkyl; and
wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment of the invention, the iodinated polymer is an iodinated polyanhydride having a backbone that comprises one or more residues of formula (II):

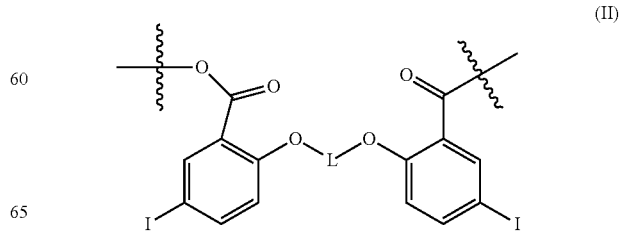

(II)

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;
each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment of the invention, the iodinated polymer is an iodinated polyanhydride having a backbone that comprises one or more residues of formula (III):

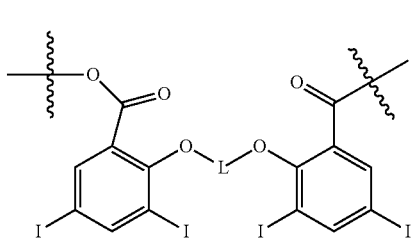

(III)

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;
each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment of the invention, the iodinated polymer is an iodinated polyanhydride having a backbone that comprises one or more residues of formula (IV):

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;
each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment of the invention, the iodinated polymer is an iodinated polyanhydride having a backbone that comprises one or more residues of formula (V):

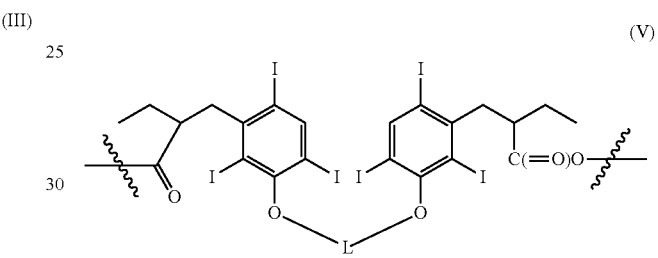

(V)

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;
each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment of the invention, the iodinated polymer is an iodinated polyanhydride having a backbone that comprises one or more residues of formula (VI):

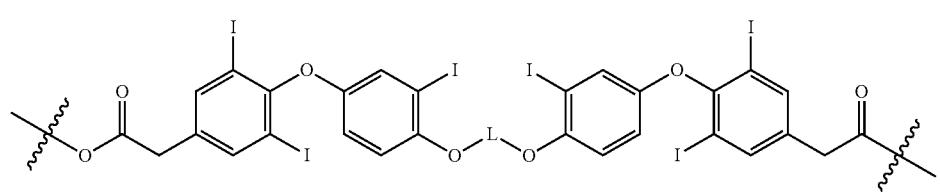

(IV)

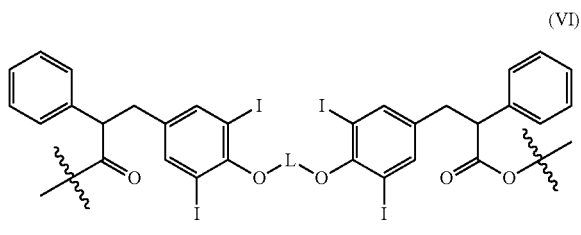

(VI)

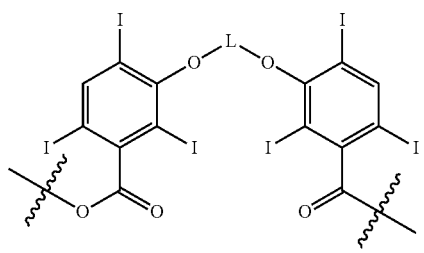

(VIII)

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—; each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment of the invention, the iodinated polymer is an iodinated polyanhydride having a backbone that comprises one or more residues of formula (VII):

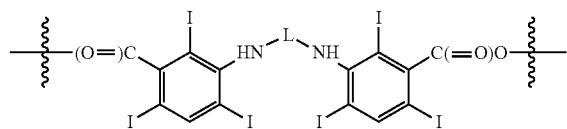

(VII)

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—; each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment of the invention, the iodinated polymer is an iodinated polyanhydride having a backbone that comprises one or more residues of formula (VIII):

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—; each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

A specific value for L is a divalent, branched or unbranched, saturated or unsaturated, hydrocarbon chain, having from 1 to 20 carbon atoms, wherein one or more of the carbon atoms is optionally replaced by (—O—) or (—NR—), and wherein the chain is optionally substituted on carbon with one or more oxo substituents.

Another specific value for L is a divalent, branched or unbranched, saturated or unsaturated, hydrocarbon chain, having from 3 to 15 carbon atoms, wherein one or more of the carbon atoms is optionally replaced by (—O—) or (—NR—), and wherein the chain is optionally substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

Another specific value for L is a divalent, branched or unbranched, saturated or unsaturated, hydrocarbon chain, having from 3 to 15 carbon atoms, wherein one or more of the carbon atoms is optionally replaced by (—O—) or (—NR—), and wherein the chain is optionally substituted on carbon with one or more oxo substituents.

Another specific value for L is a divalent, branched or unbranched, saturated or unsaturated, hydrocarbon chain, having from 3 to 15 carbon atoms, wherein the chain is optionally substituted on carbon with one or more oxo substituents.

Another specific value for L is a divalent, branched or unbranched, hydrocarbon chain, having from 4 to 8 carbon atoms, wherein the chain is optionally substituted on carbon with one or more oxo substituents.

Another specific value for L is —CH$_2$CH$_2$CH$_2$CH$_2$—.

Another specific value for L is —C(=O)(CH$_2$)$_n$C(=O)—; wherein n is 1, 2, 3, 4, 5, 6, 7, 8, 9, or 10.

In one specific embodiment the invention provides an implantable medical device that is made from a polymer that comprises a polyanhydride that has a backbone that comprises one or more residues of formula (X):

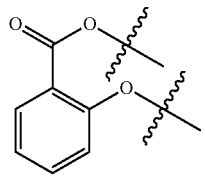

(X)

which device is coated with an iodinated polymer. In another specific embodiment, the backbone of the polyanhydride further comprises one or more residues selected from the following residues:

In another specific embodiment, the invention provides a polyanhydride that comprises units of the following formula (I):

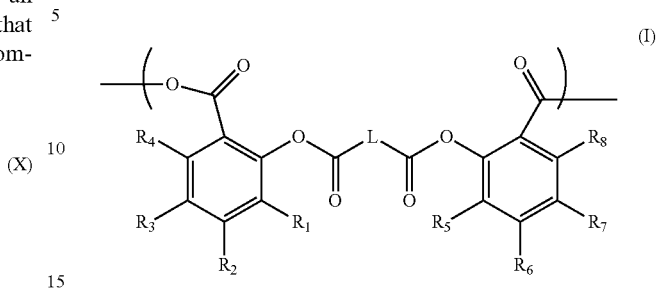

(I)

wherein:
at least one R$_1$, R$_2$, R$_3$, R$_4$, R$_5$, R$_6$, R$_7$, and R$_8$, is iodo and the rest of R$_1$, R$_2$, R$_3$, R$_4$, R$_5$, R$_6$, R$_7$, and R$_8$, are independently H or iodo; and L is a divalent, branched or unbranched, saturated or unsaturated, hydrocarbon chain, having from 1 to 20 carbon atoms, which chain can optionally be substituted on carbon with one

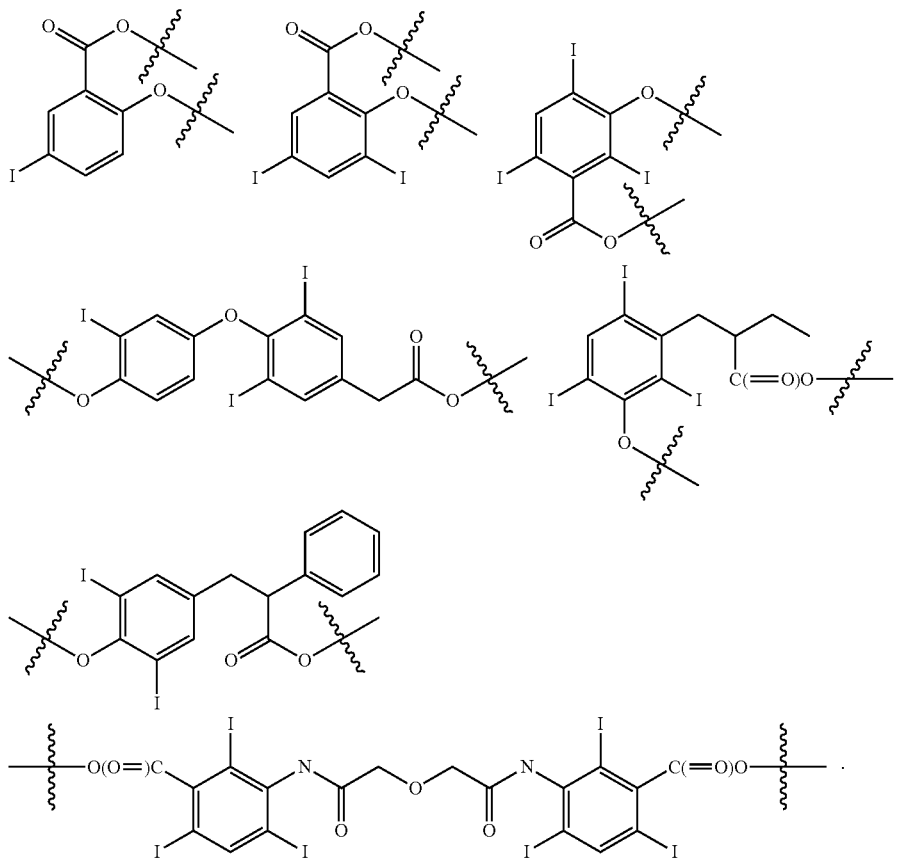

In another specific embodiment of the invention, the iodinated polymer is a copolymer that comprises residues of two or more of formulae I, II, III, IV, V, VI, VII, VIII, IX and X.

In another specific embodiment of the invention, the iodinated polymer is a copolymer that comprises residues of formula IX or X and residues of one or more of formulae I, II, III, IV, V, VI, VII, and VIII.

or more substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R) each R is independently H or (C$_1$-C$_6$)alkyl; and wherein any aryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, cyano, nitro, halo, or hydroxy.

In another specific embodiment, the invention provides a polyanhydride wherein the backbone comprises one or more residues of formula (II):

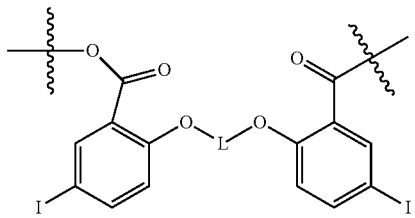

(II)

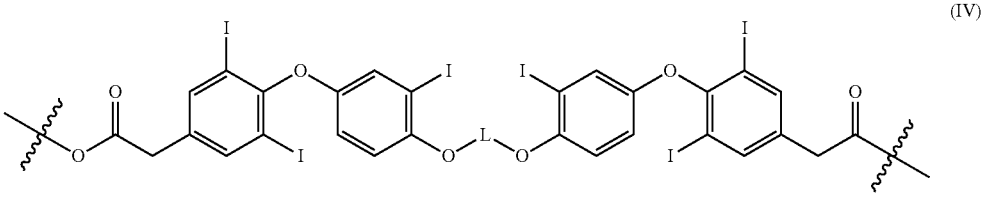

(IV)

wherein:

L is a divalent, branched or unbranched, saturated or unsaturated, hydrocarbon chain, having from 1 to 20 carbon atoms, which chain can optionally be substituted on carbon with one or more substituents selected from the group consisting of (C$_1$-C$_6$)alkoxy, (C$_3$-C$_6$)cycloalkyl, (C$_1$-C$_6$)alkanoyl, (C$_1$-C$_6$) alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;
each R is independently H or (C$_1$-C$_6$)alkyl; and wherein any aryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, cyano, nitro, halo, or hydroxy.

In another specific embodiment, the invention provides a polyanhydride wherein the backbone comprises one or more residues of formula (III):

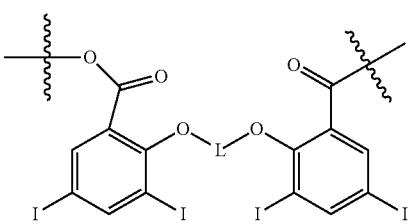

(III)

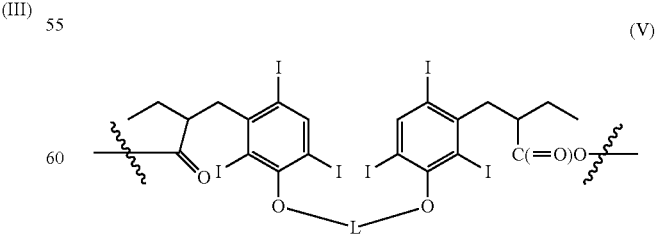

(V)

wherein:

L is a divalent, branched or unbranched, saturated or unsaturated, hydrocarbon chain, having from 1 to 20 carbon atoms, wherein:

L is a divalent, branched or unbranched, saturated or unsaturated, hydrocarbon chain, having from 1 to 20 carbon atoms, which chain can optionally be substituted on carbon with one or more substituents selected from the group consisting of (C$_1$-C$_6$)alkoxy, (C$_3$-C$_6$)cycloalkyl, (C$_1$-C$_6$)alkanoyl, (C$_1$-C$_6$) alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;
each R is independently H or (C$_1$-C$_6$)alkyl; and wherein any aryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, cyano, nitro, halo, or hydroxy.

In another specific embodiment, the invention provides a polyanhydride wherein the backbone comprises one or more residues of formula (IV):

wherein:

L is a divalent, branched or unbranched, saturated or unsaturated, hydrocarbon chain, having from 1 to 20 carbon atoms, which chain can optionally be substituted on carbon with one or more substituents selected from the group consisting of (C$_1$-C$_6$)alkoxy, (C$_3$-C$_6$)cycloalkyl, (C$_1$-C$_6$)alkanoyl, (C$_1$-C$_6$) alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;
each R is independently H or (C$_1$-C$_6$)alkyl; and wherein any aryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, cyano, nitro, halo, or hydroxy.

In another specific embodiment, the invention provides a polyanhydride wherein the backbone comprises one or more residues of formula (V):

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;

each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment, the invention provides a polyanhydride wherein the backbone comprises one or more residues of formula (VI):

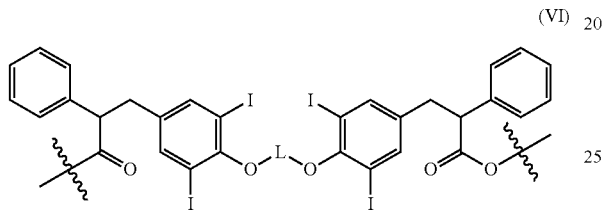

(VI)

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;

each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment, the invention provides a polyanhydride wherein the backbone comprises one or more residues of formula (VII):

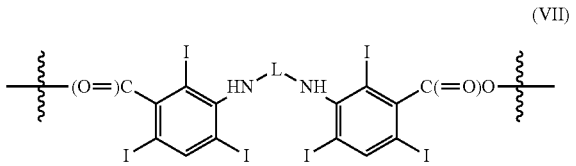

(VII)

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;

each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment, the invention provides a polyanhydride wherein the backbone comprises one or more residues of formula (VIII):

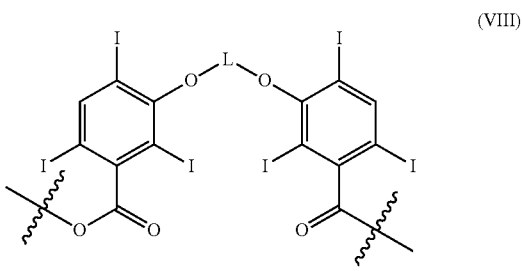

(VIII)

wherein:

L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy;

wherein one or more of the carbon atoms in the chain can optionally be replaced with —O—, -aryl-, or —N(R)—;

each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In another specific embodiment, the invention provides a polyanhydride copolymer wherein the backbone comprises residues of two or more of formulae I, II, III, IV, V, VI, VII, VIII, IX, and X.

In another specific embodiment, the invention provides a polyanhydride copolymer that comprises residues of formula IX or X and residues of one or more of formulae I, II, III, IV, V, VI, VII, and VIII.

In another specific embodiment of the invention the group L comprises iodo groups (e.g. an iodo-substituted aromatic group). One example of a possible iodinated aromatic molecule that can be incorporated into L is 5-iodoisophthaloyl chloride (see Julio C. Alvarez, et. al. Synthesis and characterization of halogen-containing polyisophthalamides. *Macromol. Chem. Phys.*, 1997, 198, 3293-3303).

Synthesis

The polyanhydrides described herein can be prepared by the method described, e.g., in Conix, Macromol. Synth., 2, 95-99 (1996) and by the methods described in International Patent Application Publication Number WO 02/009767. For example, a dicarboxylic acid can be acetylated in an excess of acetic anhydride at reflux temperatures followed by melt condensation of the resulting carboxylic acid anhydride at 160° C. for 2-3 hours to provide the polyanhydride polymers. The polymers can be isolated by precipitation into a suitable solvent (e.g. diethylether from methylene chloride). Useful polyanhydrides include both homopolymers and copolymers.

The polyanhydrides typically have average molecular weights ranging between about 1500 daltons up to about 100,000 daltons (e.g., up to about 50,000 daltons), calculated by Gel, Permeation Chromatography (GPC) relative to narrow molecular weight polystyrene standards, although higher molecular weight materials (e.g. up to at least about 100,000 daltons) are not excluded. Some aromatic polyanhydrides have average molecular weights of about 1500 daltons, up to about 20,000 daltons.

Iodinated polymers (e.g. iodinated polyanhydrides) can also be prepared by solution phase reactions such as those described by Abraham J. Domb, et. al. *Macromolecules*, 1988, 21, 1925-1929.

Iodinated polyesters and polyamides can be prepared using processes similar to those described in International Patent Application WO 2002/009768.

Figures

FIG. 1 is a block diagram of an apparatus or article 100 including an iodinated polymer 102. In some embodiments, the apparatus or article 100 is formed of a material including an iodinated polymer or a mixture of an iodinated polymer and a material such as polyester, polyanhydride, a polycarbonate, or a polyamide. In other embodiments, the apparatus or article 100 is formed of the iodinated polymer. The apparatus or article 100 is not limited to selection from a particular field of use. In some embodiments, the apparatus or article 100 is an implantable medical device. Exemplary implantable medical devices that can be fabricated, formed, or manufactured from an iodinated polymer include a stent, an orthopedic device, a bone plate, a pacemaker, a pump, a screw, a pin, a catheter, a graft, a suture, a surgical mesh, a microsphere, a film, a fiber, an intraocular lens, a surgical laser, a defibrillator, a lead or electrode for a pacemaker or defibrillator, an infusion pump, a hearing aid, a ventilator, an implantable drug pump, a cosmetic implant such as a breast or calf implant, a colonoscope, a gastroscope, an endotracheal tube, a bronchoscope, a dental prostheses, an orthodontic device, an intrauterine device, an oxygenator, a replacement joint, a bone prostheses, a cement, a replacement tendon, an artificial larynx, a ligation clip, and a ventricular-assist device.

Figure 2A:
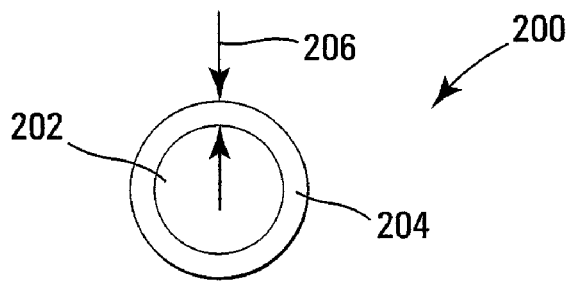
FIG. 2(a) is a cross-sectional view of an apparatus or article including a medical device and an iodinated polymer coating in accordance with some embodiments.
Figure 2B:
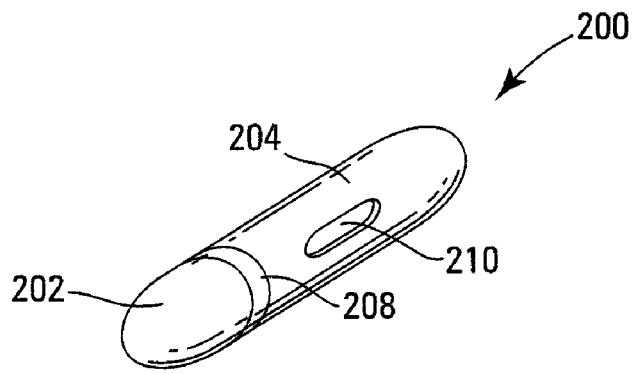
FIG. 2(b) is a perspective view of the medical device, shown in FIG. 2(a), having a surface that is partially coated with the iodinated polymer coating in accordance with some embodiments.

FIG. 2(a) is a cross-sectional view of an apparatus or article 200 including a medical device 202 and an iodinated polymer coating 204. In some embodiments, the iodinated polymer coating 204 is formed from a material including an iodinated polymer. In other embodiments, the iodinated polymer coating is formed, fabricated, or manufactured from an iodinated polymer. The iodinated polymer coating 204 has an iodinated polymer coating thickness 206. The iodinated polymer coating thickness 206 is not limited to a particular value. In some embodiments, the iodinated polymer coating thickness 206 is between about 1 mm and about 50 mm. In some embodiments, the iodinated polymer coating thickness 206 is less than about 1 mm. In some embodiments, a thickness of less than about 1 mm may not coat the medical device 202 as desired, e.g., to provide adequate radio-opacity. A thickness of more than about 50 mm may be more than required to provide the desired imaging properties and therefore unnecessarily increase the cost of fabrication of the medical device 202. The use of the iodinated polymer coating is not limited to a use in which the medical device 202 is completely coated. FIG. 2(b) is a perspective view of the medical device 200, shown if FIG. 2(a), having a surface 208 that is partially coated with the iodinated polymer coating 204. A surface is partially coated when a portion of the surface is uncoated. As shown in FIG. 2(b), a surface 210 included in the surface 208 is uncoated by the iodinated polymer coating 204.

The ability of an article to be viewed by X-ray imaging techniques can be evaluated using a variety of methods that are known. For example, it can be measured using a C-Arm protocol as described from ASTM Standard Test Methods for Radiopacity of Plastics for Medical Use Designation: F 640-79 (Reapproved 2000): Radiopacity can be determined as a specific difference between the optical density of the plastic and the background on the X-Ray film, comparing the images of the sample and a standard piece simulating the medical device or implant, or by measurements made on the image of a sample of specific thickness.

Coated articles can be prepared using any suitable coating technique, for example, by spin-coating, spray-coating, or solvent-casting.

The invention will now be illustrated by the following non-limiting Example.

EXAMPLE 1

Poly(anhydride-esters) based on iodinated versions of salicylic acid were synthesized via both melt-condensation and solution polymerization techniques to generate biomaterials offering radiopacity. The resulting iodinated polymers were found to be highly X-ray opaque when compared to poly (anhydride-esters) composed of salicylic acid alone. Molecular weight and Young's modulus of polymers prepared by melt-condensation were typically two to three times higher than polymers by solution methods. The glass transition temperatures of the polymers were dependent on the amount of iodine present; polymers containing more iodine had higher glass transition temperatures. Cytotoxicity studies using L929 mouse fibroblasts were performed for polymer-containing cell media at concentrations of 0.01 and 0.1 mg/mL and on polymer-coated surfaces. These studies indicated that iodinated salicylate-based poly(anhydride-esters) prepared by both polymerization methods are biocompatible with cells at low concentrations.

Methods to synthesize poly(anhydride-esters) comprised of salicylic acid have been described (e.g., Scheme 1). (Erdmann et al., Biomaterials 2000; 20:1941-1946; Schmeltzer et al., Polym. Bull. (Berlin) 2003; 49:441-448; and Prudencio et al., Macromolecules 2005; 38:6895-6901) These polymers degrade upon hydrolysis to release salicylic acid and the biocompatible linker molecule, which connects the two units of salicylic acid together. The drug is chemically incorporated into the polymeric backbone and not attached as a side group, (Rivas et al., J. Membr, Sci. 2001; 192:187-191; and San Roman et al., J. Biomed. Mat. Res. 1996; 32:19-27) allowing high drug loading levels. These polymers have been proven effective in vitro and in vivo (Schmeltzer et al., Biomacromolecules 2005; 6:359-367; Anastasiou et al., Journal of Polymer Science, Part A: Polymer Chemistry 2003; 41:3667-3679; Harten et al., J. Biomed. Mat. Res. 2004; 72A:354-362; and Erdmann et al., Biomaterials 2000; 21:2507-2512) with various biomedical applications.

Scheme 1. Hydrolytic degradation of poly(anhydride-ster) into salicylic acid.

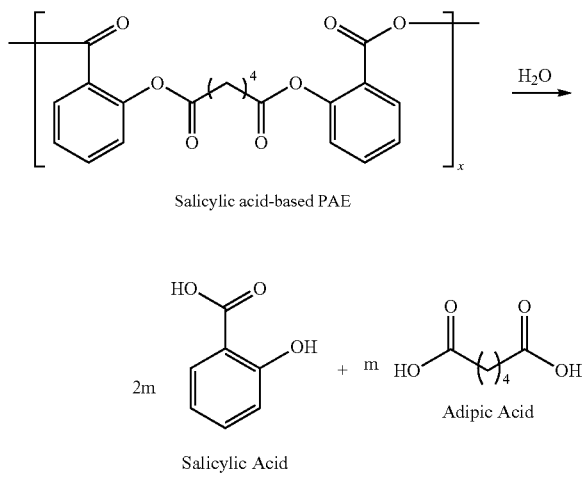

Salicylic acid-based PAE

Salicylic Acid + Adipic Acid

The polymers described herein can be derived from iodinated salicylates (Scheme 2). Salicylate derivatives that have higher melting temperatures ($T_m$) yielded polymers with corresponding higher glass transition temperatures ($T_g$). It was hypothesized that poly(anhydride-esters) derived from iodinated salicylates would not only demonstrate radiopacity but may also have enhanced mechanical properties due to the higher melting points of the iodinated derivatives. Iodinated salicylic acid-based poly(anhydride-esters) were synthesized using previously described methods (Schmeltzer et al., Polym. Bull. (Berlin) 2003; 49:441-448; Prudencio et al., Macromolecules 2005; 38:6895-6901; and Domb et al., Macromolecules 1988; 21:1925-1929) with the goal of producing polymers with both X-ray opacity and enhanced mechanical properties.

Two methods of polymerization were compared: melt-condensation (Schmeltzer et al., Polym. Bull. (Berlin) 2003; 49:441-448) and low-temperature solution polymerization (Domb et al., Macromolecules 1988; 21:1925-1929) (Scheme 2). Melt-condensation polymerization of dicarboxylic acid precursors provides polyanhydrides with relatively high molecular weights (e.g., 10,000-30,000 Da), whereas solution polymerization typically results in polymers with lower molecular weights, ranging from 5,000-10,000 Da. (Domb et al., Polym. Sci., Part A: Polym. Chem. 1987; 25:3373-3386; and Leong et al., Macromolecules 1987; 20:705-712) Polymer properties ($T_g$, $T_d$, Young's modulus) may also vary with the route of polymer synthesis. In addition, the choice of polymerization technique may be dependent on the polymer precursors. For example, low-temperature solution polymerization may be more favorable for heat sensitive peptide-based monomers. To investigate the potential differences in the resulting polymer properties, both synthetic methods were used to prepare polymers from the same monomer.

Lastly, cytotoxicity studies on L929 mouse fibroblasts were performed to evaluate polymer biocompatibility. X-ray images of the polymers were compared to bone and tissues in the body. Thermal and mechanical properties were studied in detail to ascertain the relationship between polymer properties and polymerization technique, if any.

Poly(anhydride-esters) Precursors: Diacid Synthesis (2)

Poly[1,6-bis(o-carboxyphenoxy)-hexanoate] was prepared using previously described methods. (Prudencio et al., Macromolecules 2005; 38:6895-6901) All other diacids were prepared using the following procedure (Scheme 2). In brief, the salicylate (1; 1.4 g, 10 mmol) was dissolved in a solution of tetrahydrofuran (40 mL) and pyridine (1.7 mL, 20 mmol). Adipoyl chloride (0.80 mL, 5.0 mmol) dissolved in tetrahydrofuran (10 mL) was added drop-wise to the reaction mixture at room temperature using a syringe. The reaction was stirred for 2-4 h and quenched by pouring over water and acidifying to pH 2 using concentrated hydrochloric acid. The diacid (2) was filtered, washed with deionized water (3×200 mL) and dried under vacuum at room temperature for 24 h. The diacid was recrystallized from either acetone/hexanes or diethyl ether/hexanes.

Scheme 2. Synthesis of iodinated salicylate-based poly(anhydride-esters).

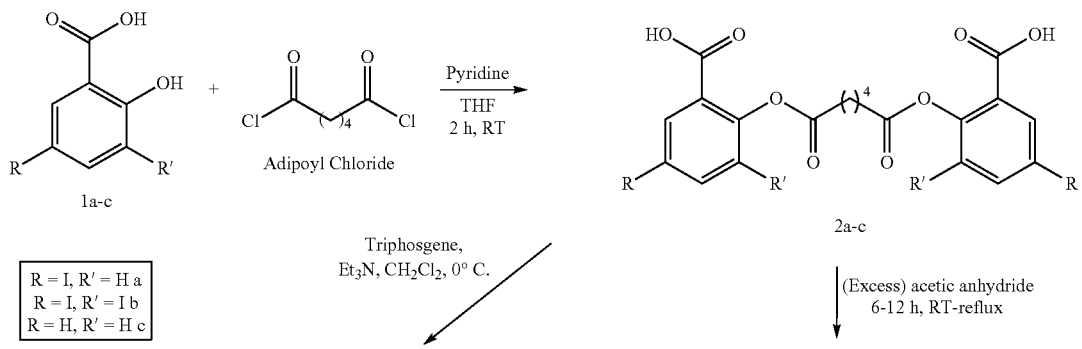

R = I, R' = H a
R = I, R' = I b
R = H, R' = H c

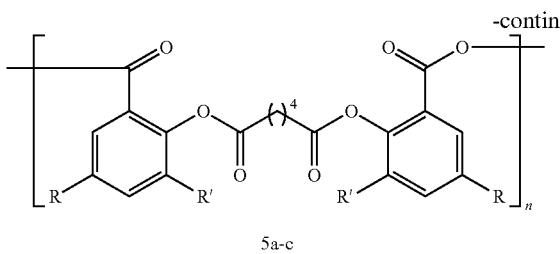

5a-c

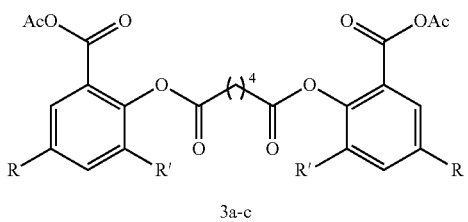

3a-c

160° C. Vacuum (<2 mm Hg) 3-6 h

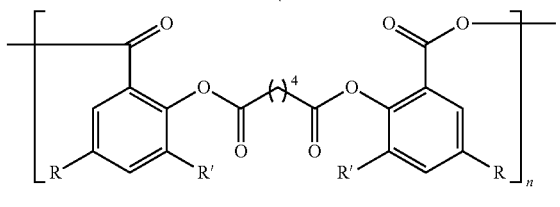

4a-c

1,6-bis(5-iodo-1,2-carboxyphenoxy)-hexanoate (2a)

Yield: 97% (white powder). $^1$H-NMR (DMSO-$d_6$): 8.20 (s, 2H, ArH), 7.98 (d, 2H, ArH), 7.05 (d, 2H, ArH), 2.63 (t, 4H, $CH_2$), 1.74 (m, 4H, $CH_2$). IR (NaCl, cm$^{-1}$): 1749 (C=O, ester), 1705 (C=O, COOH), 3579 (OH, COOH). Anal. Calcd: C, 37.69%; H, 2.53%; I, 39.82%; O. Found: C, 38.31%; H, 2.50%; I, 39.99%. $T_m$: 210-212° C.

1,6-bis(3,5-diiodo-1,2-carboxyphenoxy)-hexanoate (2b)

Yield: 98% (white powder). $^1$H-NMR (DMSO-$d_6$): 8.43 (s, 2H, ArH), 8.15 (s, 2H, ArH), 2.64 (t, 4H, $CH_2$), 1.76 (m, 4H, $CH_2$). IR (NaCl, cm$^{-1}$): 1773 (C=O, ester), 1697 (C=O, COOH), 3583 (OH, COOH). Anal. Calcd: C, 27.01%; H, 1.59%; I, 57.09%. Found: C, 27.50%; H, 1.52%; I, 56.85%. $T_m$: 202-205° C.

Acetylated Compounds Synthesis (3)

The diacid was activated by acetylation as previously outlined. (Prudencio et al., Macromolecules 2005; 38:6895-6901; Schmeltzer et al., Biomacromolecules 2005; 6:359-367; and Campo et al., Polym. Bull. 1999; 42:61-68) In brief, the diacid (2; 2 g) was added to an excess of acetic anhydride (100 mL) and stirred either at room temperature (for 2c) or heated to reflux temperature (for 2a-b) until a clear, homogeneous solution was observed (~2-12 h). The excess acetic anhydride was removed using a rotary evaporator (Buchi Model R-205 equipped with a V-800 vacuum controller, B-490 heating bath, and V-500 vacuum pump) to afford the acetylated compound (3), which was washed with diethyl ether (3×10 mL).

1,6-bis(5-iodo-1,2-carboxyphenoxy)-hexanoate Monomer (3a)

Yield: quantitative (pale yellow oil). $^1$H-NMR (DMSO-$d_6$): 8.22 (s, 2H, ArH), 8.01 (d, 2H, ArH), 7.05 (d, 2H, ArH), 2.65 (t, 4H, $CH_2$), 2.06 (s, 6H, $CH_3$), 1.76 (m, 4H, $CH_2$). IR (NaCl, cm$^{-1}$): 1814 (C=O, anhydride), 1766 (C=O, ester). $T_d$: 293° C.

1,6-bis(3,5-diiodo-1,2-carboxyphenoxy)-hexanoate Monomer (3b)

Yield: quantitative (pale orange oil). $^1$H-NMR (DMSO-$d_6$): 8.44 (s, 2H, ArH), 8.18 (s, 2H, ArH), 2.66 (t, 4H, $CH_2$), 2.30 (s, 6H, $CH_3$), 1.72 (m, 4H, $CH_2$). IR (NaCl, cm$^{-1}$): 1817 (C=O, anhydride), 1771 (C=O, ester). $T_d$: 268° C.

Melt-Condensation Polymer Synthesis (4)

For melt-condensation polymerization (Schmeltzer et al., Polym. Bull. (Berlin) 2003; 49:441-448) (Scheme 2), the acetylated compound (3a-c; 2 g) was placed in a double-necked round-bottom flask equipped with overhead stirrer (T-line Laboratory Stirrer, Model 104, Talboys Engineering, Thorofare, N.J.) and heated to 160° C. using a temperature controller (Cole-Parmer, Vernon Hills, Ill.) in a silicone oil bath under vacuum (<2 mm Hg) until the viscosity of the melt remained constant or it solidified (~2-6 h). The monomer was vigorously stirred at ~100 rpm/min using the overhead stirrer during the polymerization. When complete, the polymer was cooled to room temperature and isolated by precipitation from methylene chloride into a 20-fold excess of diethyl ether.

Melt-Condensation Poly[1,6-bis(5-iodo-1,2-carboxyphenoxy)-hexanoate] (4a)

Yield: quantitative (beige powder). $^1$H-NMR (DMSO-$d_6$): 8.22 (s, 2H, ArH), 8.01 (d, 2H, ArH), 7.05 (d, 2H, ArH), 2.65 (t, 4H, $CH_2$), 1.76 (m, 4H, $CH_2$). IR (NaCl, cm$^{-1}$): 1805, 1691 (C=O, anhydride), 1745 (C=O, ester). $M_w$: 33,000; PDI: 1.5. $T_g$: 52° C., $T_d$: 268° C. Contact angle: 72°. Young's Modulus: 2400 kPa.

Melt-Condensation Poly[1,6-bis(3,5-diiodo-1,2-carboxyphenoxy)-hexanoate] (4b)

Yield: quantitative (pale brown powder). $^1$H-NMR (DMSO-$d_6$): 8.45 (s, 2H, ArH), 8.20 (s, 2H, ArH), 2.63 (t, 4H, CH$_2$), 1.68 (m, 4H, CH$_2$). IR (NaCl, cm$^{-1}$): 1812, 1699 (C=O, anhydride), 1756 (C=O, ester). M$_w$: 4,000; PDI=1.7. T$_g$: 78° C., T$_d$: 270° C. Contact angle: 79°. Young's Modulus: 3700 kPa.

Solution Polymerization Polymer Synthesis (5)

For solution polymerization (Domb et al., Macromolecules 1988; 21:1925-1929), the diacid was directly used. Polymerization was performed under anhydrous conditions using nitrogen gas. The diacid (2; 4 g, 10 mmol) was dissolved in anhydrous methylene chloride (16 mL). Freshly distilled triethylamine (6.0 mL, 50 mmol) was added drop-wise to the reaction mixture at room temperature. The reaction was then cooled to 0° C. using an ice bath for 15 min. Triphosgene (3.4 g, 11 mmol) dissolved in anhydrous methylene chloride (15 mL) was added drop-wise to the reaction mixture at 0° C. using a syringe over 1 h. After stirring for 1.5 h, the reaction mixture was poured over diethyl ether (300 mL), the solid filtered and washed with acidified water (1 L, pH 2 with concentrated HCl). The products were dried under vacuum at room temperature.

Solution Polymerization
Poly[1,6-bis(5-iodo-1,2-carboxyphenoxy)-hexanoate] (5a)

Yield: quantitative (peach powder). $^1$H-NMR (DMSO-d$_6$): 8.08 (s, 2H, ArH), 7.99 (d, 2H, ArH), 7.03 (d, 2H, ArH), 2.64 (t, 4H, CH$_2$), 1.78 (m, 4H, CH$_2$). IR (NaCl, cm$^{-1}$): 1793, 1727 (C=O, anhydride), 1760 (C=O, ester). M$_w$: 8,000; PDI: 1.5. T$_g$: 59° C., T$_d$: 260° C., Contact angle: 67°. Young's Modulus: 1470 kPa.

Solution Polymerization Poly[1,6-bis(3,5-diiodo-1,2-carboxyphenoxy)-hexanoate] (5b)

Yield: quantitative (pale pink powder). $^1$H-NMR (DMSO-d$_6$): 8.43 (s, 2H, ArH), 8.18 (s, 2H, ArH), 2.67 (t, 4H, CH$_2$), 1.73 (m, 4H, CH$_2$). IR (NaCl, cm$^{-1}$): 1795, 1732 (C=O, anhydride), 1765 (C=O, ester). M$_w$: 8,000; PDI: 1.7. T$_g$: 68° C., T$_d$: 220° C. Contact angle: 46°. Young's Modulus: 190 kPa.

Degradation of Polymer-Coated Coverslips

Microscope glass coverslips were coated with polymer (~10 mg/coverslip) and UV-sterilized as described above, seeded with cell media (2 mL) in a 12-well plate (Fisher Scientific, Fair Lawn, N.J.) and incubated at 37° C. for 3 days. At predetermined time points (24 h, 48 h and 72 h), aliquots of media were removed and analyzed using UV/vis spectrophotometry to determine the amount of free drug (1a-c) in the media. The amounts were calculated with respect to calibration curves of standard solutions of each compound (1a-c).

Polymer Synthesis and Physiochemical Characterization

Iodinated salicylic acid-based poly(anhydride-esters) were successfully prepared via both melt-condensation and low temperature solution polymerization methods. The first step in the synthesis of the polymers was to prepare the diacid (2; Scheme 2). This compound was made by directly coupling the iodinated salicylic acid derivative (1) to adipoyl chloride in an appropriate solvent (THF) and base (pyridine) at room temperature. (Schmeltzer et al., Polym. Bull. (Berlin) 2003; 49:441-448; and Prudencio et al., Macromolecules 2005; 38:6895-6901) The pyridine first deprotonates the iodinated salicylate (1) and secondly, acts as a catalyst to form an acyl pyridinium ion, (Fersht et al., Am. Chem. Soc. 1970; 92(18): 5442-5452) which reacts with the free phenolate of the iodinated salicylate to form the diacid (2). The carboxylic acid group on the iodinated salicylic acid (1) need not be protected as the acyl pyridinium ion reacts faster with alcohols than acyl chlorides. (Fersht et al., Am. Chem. Soc. 1970; 92(18):5442-5452; Hoefle et al., Angew. Chem., Int. Ed. Engl. 1978; 17:569-583) The products (2a-c) obtained using this method are very pure as determined by NMR and elemental analysis, and further purification was not necessary based on the large solubility differences between the reaction byproducts/starting materials and the diacid (2) formed. (Schmeltzer et al., Polym. Bull. (Berlin) 2003; 49:441-448) Percent yields for both the 5-iodosalicylic acid-based diacid (2a) and the 3,5-diiodosalicylic acid-based diacid (2b) were quantitative. The melting point for the 5-iodosalicylic acid-based diacid (2a) was 210-212° C., whereas the melting point for the 3,5-diiodosalicylic acid-based diacid (2b) was 202-205° C.

After diacid synthesis was complete, the diacids were used to prepared the poly(anhydride-esters) via melt-condensation and solution polymerization (Scheme 2). As in common melt-condensation polymerization procedures, (Schmeltzer et al., Polym. Bull. (Berlin) 2003; 49:441-448; Prudencio et al., Macromolecules 2005; 38:6895-6901; Schmeltzer et al., Biomacromolecules 2005; 6:359-367; Campo et al., Polym. Bull. 1999; 42:61-68; and Gopferich, Biomaterials 1996; 17:103-114) the diacids (2a-c) were activated using an excess of acetic anhydride to form the polymer precursor or monomer (3a-c), which is then polymerized at elevated temperatures (i.e., 160° C.) under vacuum via the removal of the melt-condensation byproduct, acetic anhydride.

For solution polymerization, (Domb et al., Macromolecules 1988; 21:1925-1929; and Leong et al., Macromolecules 1987; 20:705-712) the diacids (2a-c) were used directly in the presence of base (e.g., triethylamine), in the appropriate solvent (e.g., methylene chloride) and a coupling reagent (triphosgene) (Domb et al., Macromolecules 1988; 21:1925-1929; Leong et al., Macromolecules 1987; 20:705-712; Eckert et al., Angew. Chem. 1987; 99(9):922-923; and Le Nest et al., Electrochim. Acta 1992; 37:1585) (2a-c) to give the resulting polymers (5a-c). This method of polymerization can be used to prepare polymers from polymer precursors that are heat sensitive.

After all polymers were synthesized, the materials were characterized by $^1$H NMR, FTIR, GPC, TGA, DSC and DMA. Some of these characteristics are provided in Table 1. Several trends are observed for melt-condensation versus solution-made poly(anhydride-esters). First, the molecular weights for melt-condensation polymerization products (4a-c) were typically higher than for solution polymerization (5a-c). Solution polymerization typically results in polymers with lower molecular weights than that of melt-condensation polymerization products due to the strict stoichiometric control needed for the polymerization to be efficient. (Leong et al., Macromolecules 1987; 20:705-712; Domb et al., Advances in Polymer Sciences: Springer-Verlag; 1993) A higher polydispersity index was observed for melt-condensation (4a-c) versus solution (5a-c) polymers. The polydispersity is also reflected in the $^1$H NMR spectra: melt-condensation polymers (4a-c) had much broader peaks, with respect to the solution polymerization polymers (5a-c), which had much sharper peaks in the NMR spectra.

Glass transition temperatures (T$_g$) varied with the number of iodine atoms per salicylic acid molecule; T$_g$ values increased with increased numbers of iodine atoms. For example, polymer 4c contains no iodine and displays a glass transition temperature of 46° C., whereas the polymers based on 5-iodosalicylic acid (4a) (i.e., one iodine per salicylate) and 3,5-diiodosalicylic acid (4b) (i.e., two iodine atoms per salicylate) had higher glass transition temperatures (52° C. and 78° C., respectively). A similar tendency was observed for Young's modulus when comparing polymers obtained from melt-condensation polymerization methods (4a-c); increasing the number of iodine atoms increased the Young's modulus. In general, the Young's modulus of melt-condensation polymerization products (4a-c) were higher than the corresponding solution polymerization products (5a-c).

Scanning electron microscopy (SEM) images were obtained of thin polymer films coated on microscope glass coverslips. Generally, the melt-condensation polymers (4a-c) had smoother surfaces compared with the corresponding solution polymers (5a-c).

Following physiochemical characterization, polymers were pressed into circular disks (13 mm diameter×1 mm thickness) and analyzed via X-ray. Iodinated salicylic acid based-poly(anhydride-esters) disks 4a-b and 5a-b can be readily observed using standard clinical X-ray techniques. Using these homopolymers or copolymers of the iodinated salicylate-based polymers with other polymers, such as those with therapeutic capabilities (e.g., 4c and 5c), as potential implant coatings or in the production of biomaterials, is expected to be highly advantageous to physicians.

Additional interpretation of the radiopacity is outlined in Table 1. Polymers 4a-c and 5a-b were examined under a clinical X-ray machine (C-Arm) and ranked from 1 to 6, (WWWASTMF640-79. Standard Test Methods for Radiopacity of Plastics for Medical Use. ASTM International:West Conshohocken, Pa.) with 6 being most visible and 1 being invisible. Polymer disks containing no iodine (4c) were not visible, whereas the 3,5-diiodosalicylic acid-based polymer made by melt-condensation (4b) was most visible. Generally, the solution polymerization products, (5a-b), were less X-ray visible compared to the corresponding melt-condensation polymers, (4a-b). This difference could be attributed to the differences in the polydispersity indices of the polymers (see Table 1), which influence the polymer's packing efficiency. The broader the polydispersity, the better the packing efficiency; (Antonietti et al., Langmuir 2000; 16:7634-7639) denser materials absorb more X-rays and appear to be more radiopaque under a clinical X-ray machine. Moreover, the iodinated salicylic acid-based poly(anhydride-esters) 4a-b and 5a-b were found to be significantly more X-ray opaque than bones or tissue in the hand.

TABLE 1

Characterization of salicylic acid-based poly(anhydride-esters) and iodinated salicylic acid-based poly(anhydride-esters) prepared by melt-condensation (4a-c) and solution polymerization (5a-c). X-ray opacity is ranked from 1 (not visible) to 6 (best visual).

| Drug | Polymer | $M_w$ | PDI | $T_g$ (° C.) | $T_d$ (° C.) | Young's Modulus (kPa) | X-Ray Opacity |
|---|---|---|---|---|---|---|---|
| Salicylic Acid, 1c | 4c | 31,800 | 1.8 | 46 | 290 | 1500 | 1 |
|  | 5c | 10,000 | 1.1 | 23 | 240 | 330 | — |
| 5-Iodosalicylic Acid, 1a | 4a | 33,000 | 1.5 | 52 | 260 | 2400 | 2 |
|  | 5a | 8,000 | 1.5 | 59 | 260 | 1470 | 3 |
| 3,5-Diiodosalicylic Acid, 1b | 4b | 7,700 | 1.7 | 78 | 270 | 3700 | 6 |
|  | 5b | 4,000 | 1.4 | 68 | 220 | 190 | 5 |

Cell Compatibility: Polymer-Containing Media

For testing biocompatibility of the polymers, cytotoxicity experiments were performed using L929 mouse fibroblasts to examine cellular response using two methods: culturing cells in polymer-containing media (0.1 and 0.01 mg/mL) and culturing cells directly on polymer-coated glass coverslips. Both studies were performed over a three day time period, in which cell proliferation and morphology were measured. The chosen concentrations of polymer in media (0.01 and 0.1 mg/mL were based on standard cytotoxicity protocols. (Schmeltzer et al., Biomacromolecules 2005; 6:359-367)

Iodinated salicylic acid-based polymers (4a-b and 5a-b) and salicylic acid-based polymers (4c and 5c) cytocompatibility were tested by monitoring cell proliferation and morphology. L929 mouse fibroblast cells were seeded in media containing polymers 4a-b and 5a-b at 0.01 and 0.1 mg/mL polymer concentrations. L929 fibroblast cells are a standard cell type for cytocompatibility testing as recommended by ASTM, (Duncan et al., New Products and Standards In Biomaterials Science. New York: Elsevier Academic Press; 2004) and three days was chosen as the incubation period to allow for the completion of at least one cell cycle.

The cell proliferation profile for 3 days in the presence of the lower (0.01 mg/mL) polymer concentration was determined. On day 1, cell numbers in the media containing polymer show successful attachment to the culture plate and did not show significant difference to the cells in controls at any time, except the media containing polymer 5b. At day 2 and 3, cells showed normal growth cycles for all samples, cell numbers increased more than two-fold and indicated at least one growth cycle occurrence per day. For the cells in media containing polymer 5b, lesser cell numbers attached, but cell numbers increased showing a normal growth cycle.

Cell attachment and proliferation at higher polymer concentrations (0.1 mg/mL) in media was also determined. Cells in media containing the salicylic acid-based polymer (4c) and the 5-iodosalicylic acid-based polymers (4a, 5a) exhibit a positive growth profile over the 3 days, and cell numbers were within standard deviation of the DMSO control on day 1 and 3. Slightly higher cell numbers were noted in the solution-polymerized 5-iodosalicylic acid-based polymer, (5a). Cells in the presence of the 3,5-diiodosalicylic acid-based polymers (4b, 5b) exhibit significantly low cell numbers for 3 days and did not show positive growth profiles ($p<0.05$).

Cellular morphology in media containing polymers 4a-b and 5a-b at higher polymer concentrations (0.1 mg/mL) and controls (DMSO and media only) on day 3 was also determined. In general, cells are successfully attached and spread with a normal stellate morphology for all samples. Cell images in the media alone showed similar morphology with that of the media containing DMSO. Cell images in the polymer 5c showed similar morphology with that of polymer 4c. Although cells in 5b showed less cell attachment, cells spread and proliferated in a normal manner. Overall, good biocompatibility of iodinated salicylic acid-based was observed at low concentrations of polymers in the cell media.

Cells on day 3 for each sample were examined, and normal stellate morphology was found for the polymers, 4a, 4c, 5a, without difference with the controls, but a less amount of cells with rounded morphology were found on polymers 4b and 5b. Based upon the results of this study, cells on the 5-iodosalicylic acid-based polymers (4a and 5a) are deemed biocompatible, but the 3,5-diiodosalicylic acid-based polymers (4b and 5b) were less biocompatible for this certain concentration.

Cell Compatibility Polymer-Coated Surfaces

For biocompatibility studies in polymer-containing media, the results exhibited different cell proliferation corresponding to the melt-condensation and solution polymerization methods. For further analysis, fibroblasts were incubated on polymer-coated surfaces for 3 days, and morphology and cell numbers were evaluated. While coating the coverslips with polymer solution (100 mg/mL), humidity was controlled as less than 20% in air to generate homogenous surfaces.

Cell numbers on all polymer surfaces were statistically the same with controls on day 1. Day 1 observations revealed that cells successfully attached and proliferated for at least 24 hours. Cell proliferation on salicylic acid-based polymers (4c and 5c) and control surfaces show normal growth profile, but cells on other polymers (4a-c, 5a-b) have negative growth profiles on days 2 and 3. 5-Iodosalicylic acid-based polymers 4a and 5a show relatively higher cell numbers compared to 3,5-diiodsalicylic acid-based polymers, 4b and 5b. Among the iodinated polymers (4a-b, 5a-b), a difference correlated to the polymerization process was not observed. Interestingly, cells on the salicylic acid-based polymer 5c (solution polymerization) showed statistically higher proliferation than cells on polymer 4c (melt-condensation method).

Cellular morphology on the polymer surfaces was also observed. As in agreement with cell proliferation profiles, only cells on 5c and the control surfaces showed normal stellate morphology, otherwise cells have a rounded appearance with a much lower amount of cells present. The iodinated polymers showed less biocompatibility at higher concentrations. A possible reason for the lowered compatibility on day 2 and 3 may result from high polymer concentration (100 mg/mL) on the cell culturing system. This was further analyzed by degrading the polymer surfaces to determine the concentration of free drug (1a-c) released into the media during the time period of the cytotoxicity assay. Cells on the surfaces of polymer 5b show similar morphology with 5a, a rounded cell morphology.

Degradation of Polymer-Coated Coverslips.

In Table 2, the maximum amount of free drug, 1a-c, that could be released from each polymer is listed. The maximum amount of 1a-c that can be released from the corresponding polymers, 4a-c or 5a-c, is much larger for the polymer-coated coverslips than in the polymer-containing media. A much larger local concentration of free drug (1a-c) in media is possible with the coated coverslips, which may explain the results obtained for cytotoxicity in this testing system.

TABLE 2

Maximum possible release of free drug (1a-c) upon complete hydrolysis of polymer backbone.

| Drug | Polymer | Maximum release[1] | Maximum release[2] | Maximum release[3] |
| --- | --- | --- | --- | --- |
| Salicylic Acid, 1c | 4c/5c | 5.0 | 0.10 | 0.010 |
| 5-Iodosalicylic Acid, 1a | 4a/5a | 7.0 | 0.14 | 0.014 |
| 3,5-Diiodosalicylic Acid, 1b | 4b/5b | 7.9 | 0.16 | 0.016 |

[1]Maximum release of 1a-c from coated coverslip (mg).
[2]Maximum release of 1a-c from 0.1 mg/mL polymer-containing media (mg).
[3]Maximum release of 1a-c from 0.01 mg/mL polymer-containing media (mg).

The amount of free drug (1a-c) in media was analyzed by UV/vis spectrophotometry. The results can be seen in Table 3. The cumulative release of salicylic acid (1c) from coated coverslips with polymers 4c and 5c were 7.8 and 4.2 mg/mL, respectively. The cumulative release of the iodinated derivatives of salicylic acid (1a-b) were much larger, ~35% released from each polymer, 4a-b and 5a-b after 3 days. The concentrations of the polymers (4a-c, 5a-c) and free drugs (1a-c) in media are significantly higher in the presence of polymer-coated glass coverslips than for the polymer-containing media at 0.1 and 0.01 mg/mL concentrations. This result is consistent with results for the cell compatibility in polymer-containing media. The cell numbers for polymer-coated glass coverslips were much lower than those calculated for polymer-containing media. This effect is attributed to the high concentration of free drug (1a-c) in media for the polymer-coated glass coverslips, which may affect cell attachment and proliferation.

TABLE 3

Cumulative release of free drug (1a-c) after incubation in cell media at 37° C. after day 1, 2 and 3.

| Polymer | Day 1 Release of Drug, 1a-c (%) | Day 2 Release of Drug, 1a-c (%) | Day 3 Release of Drug, 1a-c (%) |
| --- | --- | --- | --- |
| 4c | 0.19 | 0.38 | 7.8 |
| 5c | 0.21 | 0.38 | 4.2 |
| 4a | 9.0 | 27 | 36 |
| 5a | 13 | 26 | 36 |
| 4b | 12 | 22 | 33 |
| 5b | 12 | 25 | 35 |

Materials

All solvents and reagents were purchased from Fisher Scientific (Pittsburgh, Pa.), and all other fine chemicals were purchased from Sigma-Aldrich (Milwaukee, Wis.).

Spectroscopic Methods

Proton nuclear magnetic resonance ($^1$H NMR) spectra of the products were performed using a Varian 200 MHz, 300 MHz, or 400 MHz spectrophotometer. The chosen deuterated solvent was dimethyl sulfoxide-$d_6$, which was also used as the internal reference. Fourier-transform infrared (FTIR) absorption spectra of the products were recorded using a Thermo Nicolet/Avatar 360 FT-IR spectrometer by solvent-casting samples using acetone or methylene chloride onto sodium chloride plates. Melting points were determined using a Model 1002D Manual Mel-temp apparatus (Barnstead/Thermolyne, Dubuque, Iowa). Elemental analyses were provided by QTI (Whitehouse, N.J.). Static contact angles were measured by dropping deionized water onto pressed polymer disks using a Ramé-Hart Instrument Company (Mountain Lakes, N.J.) Standard Goniometer Model Number 250-00 outfitted with a Dell Dimension 3000 computer with DROPimage Advanced software.

Molecular Weight Analysis

Molecular weights ($M_w$) and polydispersity indices (PDI) were determined using gel permeation chromatography (GPC) with respect to polystyrene standards (Polymer Source Inc., Dorval, Canada). The Perkin-Elmer LC system was equipped with a Series 200 refractive index detector, a Series 200 pump, and ISS 200 autosampler. A Dell OptiPlex GX110 computer with Perkin-Elmer TurboChrom 4 software was used for collection and processing of the data and for the automation of the GPC analyses using a Perkin-Elmer Nelson 900 Series Interface and Perkin-Elmer Nelson 600 Series Link. The samples (~5 mg/mL) were dissolved in methylene chloride and filtered using 0.45 μm pore size poly(tetrafluoroethylene) (PTFE) syringe filters (Nalge Nunc International, Rochester, N.Y.) and placed in sample vials to be injected into the system. Molecular weights were determined using a Jordi DVB mixed-bed GPC column (7.8×300 mm, Alltech, Deerfield, Ill.).

Thermo/Mechanical Analysis

Thermal analyses and mechanical properties were measured using a Perkin-Elmer system consisting of a Pyris 1 differential scanning calorimeter (DSC), thermogravimetric analyzer (TGA) and dynamic mechanical analyzer (DMA) with TAC 7/DX instrument controllers or Thermal Advantage system consisting of a differential scanning calorimeter (DSC) Q200 and thermogravimetric analyzer (TGA) Q50. A Dell Optiplex GX110 computer equipped with Perkin-Elmer Pyris software or IBM ThinkCentre computer equipped with Thermal Advantage Universal Analysis software were used for data collection and processing. The glass transition temperature ($T_g$) was determined using samples (5-10 mg) under nitrogen gas heating from −10° C. to 200° C. at a heating rate of 10° C./min and cooling down to −10° C. at a rate of 10° C./min with a minimum of two cycles. The $T_g$ was calculated as half $C_p$ extrapolated. For thermogravimetric analysis, samples (5-10 mg) were heated under nitrogen gas from 25° C. to 400° C. at a rate of 10° C./min, the decomposition temperature ($T_d$) was calculated as the onset of thermal decomposition. Young's modulus was determined on pressed disks by dynamic mechanical analysis from the slope of the linear portion of the static stress versus strain curve. The DMA method includes applying constant pressure from 0 mN to 8000 mN at a rate of 500 mN/min at 22° C.

Disc Formation

Polymer disks were prepared from powdered samples (~160 mg) using Carver model #3853 bench-top hydraulic press (Carver Inc., Wabash, Ind.) applying pressure of 10,000 psi for 5 minutes at room temperature to afford disks with dimensions of 13 mm in diameter and 1 mm in thickness using a stainless steel mold.

Measurement of Radiopacity

Radiopacity of polymer disks was measured using a clinical X-ray machine according to Method B of the ASTM F 640-79 Standard Test Methods for Radiopacity of Plastics for Medical Use. (ASTMF640-79. Standard Test Methods for Radiopacity of Plastics for Medical Use. ASTM International:West Conshohocken, Pa.) In brief, polymer disks were placed on the stage of the C-arm and blindly ranked from 1 to 6, where 6 is the darkest (e.g., most X-ray opaque) and compared to a standard aluminum-step wedge. The C-arm setup consisted of the X-ray instrument equipped with a 2.5 mm aluminum filtration set at 70 kV with a 10-20 mA current for 15 ms.

Electron Microscopy

Microscope glass coverslips (Fisher Scientific, Fair Lawn, N.J.) were coated with polymer (10 wt % in methylene chloride) for scanning electron microscopy (SEM) studies using a Badger Model 350-3 airbrush system (Badger Air-Brush Co., Franklin Park, Ill.) The coverslips were spray-coated with polymer solution until a visually uniform coating was observed (~30 s). The coatings were allowed to dry for 12 h at room temperature, then 12 h under vacuum at 25° C. to ensure full removal of solvent. The amount of coated polymer was evaluated by weighing substrates both before spraying and after drying. The coating thickness was measured using a digital micrometer/caliper (Fowler ProMax, Newton, Mass.). SEM was performed by first mounting samples (spray-coated polymer on microscope glass coverslips) onto the appropriate holder using nonconductive adhesive tabs (Electron Microscopy Sciences, Fort Washington, Pa.). The samples were then coated with an amalgam of Au—Pd using a sputter coater for 60 s at room temperature (Balzers SCD 004 Sputter Coater (BAL-TEC, Tucson, Ariz.). An Amray 1830 I scanning electron microscope (Amray, Inc., Bedford, Mass.) equipped with a Dell Workstation computer using FlashBus FBG 4.2 software was used to obtain the images.

Cell Compatibility Polymer-Containing Media

For testing polymer biocompatibility, cytotoxicity studies of the iodinated salicylic acid-based polymers (4a-b and 5a-b) and salicylate-based polymers (4c and 5c) were tested in two different ways: culturing cells in media containing the polymers and on polymer-coated surfaces. Cellular morphology and proliferation was investigated using both methods.

To evaluate cell-compatibility in media containing polymers, each polymer (4a-c and 5a-c) was dissolved in dimethyl sulfoxide (10 mg/mL; DMSO, Sigma, St. Louis, Mo.) as a stock solution, and then diluted with cell culture media to two concentrations (0.01 mg/mL and 0.1 mg/mL). Cell media was composed of Dulbecco's Modified Eagle's Medium (Sigma) supplemented with 10% fetal bovine serum (Atlanta Biologicals, Lawrenceville, Ga.), 1% v/v glutamate (Sigma) and 50 U/mL penicillin/streptomycin (Sigma). Media containing polymer was added into a 24-well plate (Fisher, Fair Lawn, N.J.), and media without the polymer and DMSO-containing media were used as the controls.

L929 mouse fibroblasts were obtained from Dr. K. E. Schmalenberg (Rutgers University, NJ). Cells stored in liquid nitrogen were thawed in a 37° C. water bath (Precision 180 Series, Thermo, Waltham, Mass.) for 5 minutes and cultured in a 25 $cm^2$ flask (Fisher) in a humidified incubator with 95% humidifier air and 5% $CO_2$ (ThermoForma, Steri-Cycle $CO_2$ Incubator, Franklin, Mass.). When cells showed 80% confluency in the flask, media was removed by vacuum, and trypsin (0.02 mg/mL, Sigma) solution added. Trypsin incubation was done at 37° C. in an incubator for 5 minutes, allowing cells to detach from flask surface. Cell pellets were obtained through centrifugation at 2000 RPM for 2 min (General Purposes Centrifuge; 5682 3L GP, Thermo, Franklin, Mass.). L929 fibroblasts were seeded into media containing polymers 4a-c and 5a-c as $5 \times 10^4$ cells per well and cultured for 3 days. All experiments were performed in triplicate.

Cellular morphology in polymer-containing media was observed and documented with random images using light microscopy (Olympus, IX81, Center Valley, Pa.) at 20× original magnification over the time period. At each time point (days 1, 2 and 3), cell numbers were measured by staining live cells with Calcein AM. Cells were washed twice with phosphate buffered saline (pH 7.4; MP Biomedical, Aurora, Ohio) and incubated with 8 μM of Calcein AM (Molecular Probe, Carlsbad, Calif.) solution for 40 min at 4° C. Calcein AM enables live cells to fluoresce at 485 nm. After 40 min of incubation, fluorescent intensity was measured using Cytofluor® (Applied Biosystems, Series 4000, Woodinville, Calif.), and cell numbers calculated based upon a standard curve.

Cell Compatibility Polymer-Coated Surfaces

Further biocompatibility testing of the iodinated polymers (4a-b and 5a-b) were performed by culturing cells on polymer-coated glass coverslips. Iodinated salicylic-based polymers (4a-b, 5a-b) and salicylic acid-based polymers (4c and 5c) were dissolved in methylene chloride at a concentration of 100 mg/mL. Two to three drops of polymer solution were added onto glass coverslips (18 mm diameter, 0.15 mm thickness; Fisher Scientific, Pittsburgh, Pa.) and homogenously coated using spin-coater at 2000 rpm for 30 s in less than 20% of humidity (Headway Research, Inc., Garland, Tex.). Polymer-coated coverslips were sterilized under UV-light at 254 nm for 900 s using a Spectrolinker XL-1500 UV crosslinker (Spectronics Corp., Westbury, N.Y.) and placed onto a 12-well tissue culture plate (Fisher Scientific, Fair Lawn, N.J.). Blank coverslips (uncoated) were used as a control. Fibroblasts were maintained in the same method described above, and cells were added to polymer-coated surfaces with $1 \times 10^5$ cells/well.

Cellular morphology and proliferation on polymer-coated surfaces were investigated under light-microscopy. At specific time points (days 1, 2 and 3), multiple random images were taken and cell numbers were counted using the count/size menu in MicroSuite™ imaging software (Olympus, Soft Imaging Program, Center Valley, Pa.).

Cell proliferation for both media containing polymers and polymer-coated surfaces was compared to the controls and statistically analyzed using a Student's t-test at 95% confidence levels using Microsoft EXCEL program (Microsoft Office 2003, Microsoft, Redmond, Wash.).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An implantable device that comprises a biodegradable iodinated polymer which comprises an iodinated polyanhydride having a backbone that comprises one or more of the following residues:

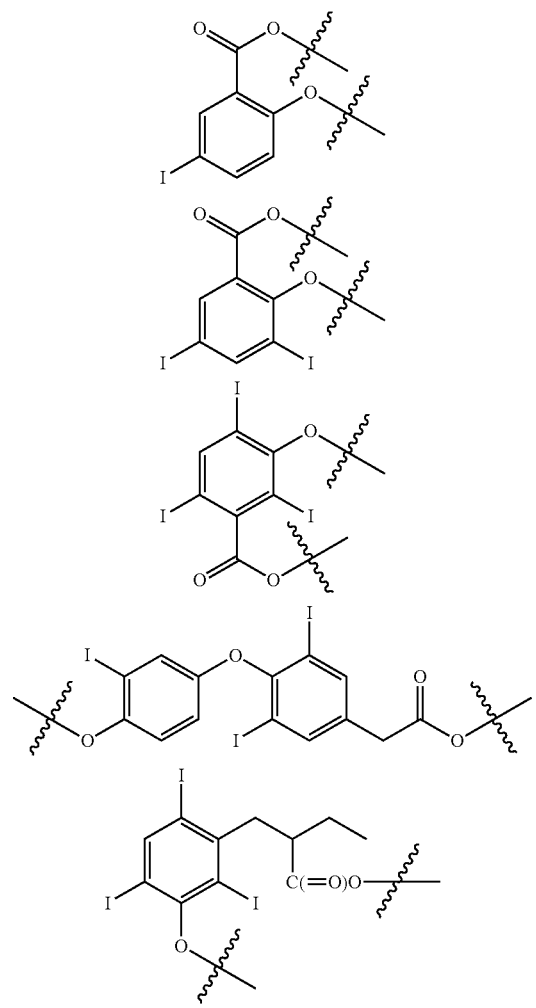

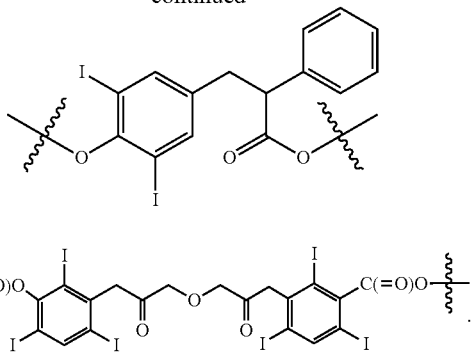

2. An implantable device that comprises a biodegradable iodinated polymer which comprises an iodinated polyanhydride having a backbone that comprises a residue of one or more of the following amino acids:

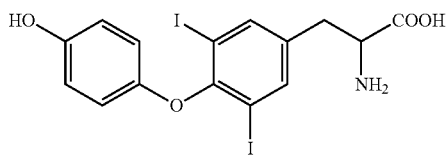

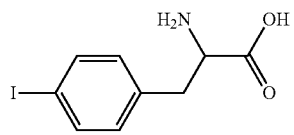

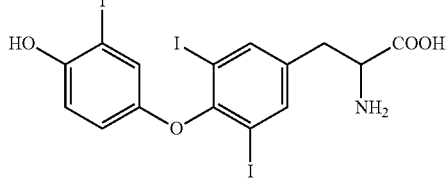

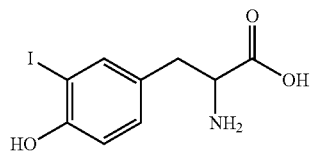

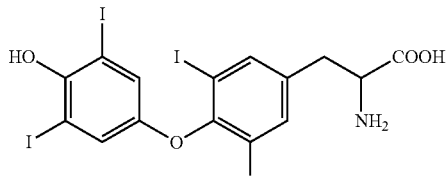

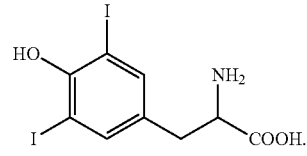

3. The implantable device of claim 1 which comprises an iodinated polyanhydride having a backbone that comprises one or more residues of formula (II):

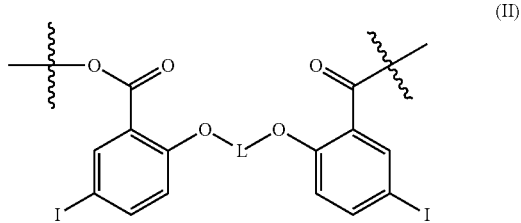

(II)

heteroaryloxy; wherein one or more of the carbon atoms in the chain can optionally be replaced with —O—, -aryl-, or —N(R)—; each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

5. The implantable device of claim 1 which comprises an iodinated polyanhydride having a backbone that comprises one or more residues of formula (IV):

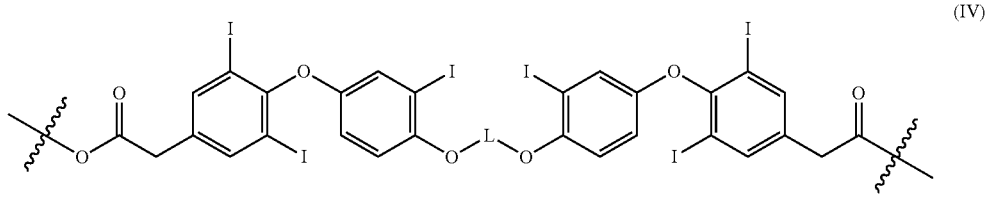

(IV)

wherein:
  L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy; wherein one or more of the carbon atoms in the chain can optionally be replaced with —O—, -aryl-, or —N(R)—; each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

wherein:
  L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy; wherein one or more of the carbon atoms in the chain can optionally be replaced with —O—, -aryl-, or —N(R)—;
  each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

4. The implantable device of claim 1 which comprises an iodinated polyanhydride having a backbone that comprises one or more residues of formula (III):

6. The implantable device of claim 1 which comprises an iodinated polyanhydride having a backbone that comprises one or more residues of formula (V):

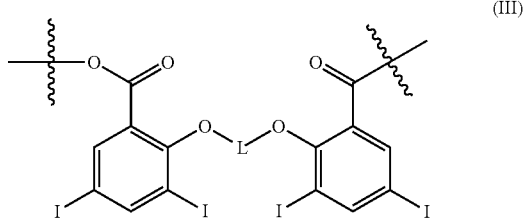

(III)

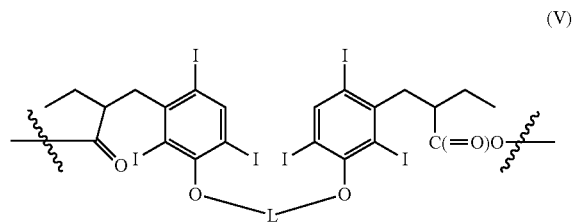

(V)

wherein:
  L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and wherein:
  L is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy; wherein one or more of the carbon atoms in the chain can optionally be replaced with —O—, -aryl-, or —N(R)—; each R is independently H or (C$_1$-C$_6$)alkyl; and wherein any aryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, cyano, nitro, halo, or hydroxy.

7. The implantable device of claim 1 which comprises an iodinated polyanhydride having a backbone that comprises one or more residues of formula (VI):

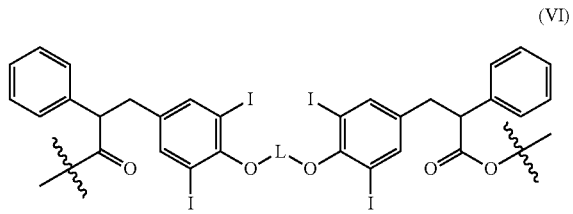

(VI)

wherein:

L is a divalent, branched or unbranched, saturated or unsaturated, hydrocarbon chain, having from 1 to 20 carbon atoms, which chain can optionally be substituted on carbon with one or more substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy; wherein one or more of the carbon atoms in the chain can optionally be replaced with —O—, -aryl-, or —N(R)—; each R is independently H or (C$_1$-C$_6$)alkyl; and wherein any aryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, cyano, nitro, halo, or hydroxy.

8. The implantable device of claim 1 which comprises an iodinated polyanhydride having a backbone that comprises one or more residues of formula (VIII):

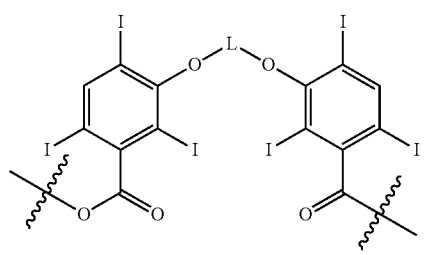

(VIII)

wherein:

L is a divalent, branched or unbranched, saturated or unsaturated, hydrocarbon chain, having from 1 to 20 carbon atoms, which chain can optionally be substituted on carbon with one or more substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy; wherein one or more of the carbon atoms in the chain can optionally be replaced with —O—, -aryl-, or —N(R)—; each R is independently H or (C$_1$-C$_6$)alkyl; and wherein any aryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, cyano, nitro, halo, or hydroxy.

9. The implantable device of claim 6 wherein L is a divalent, branched or unbranched, saturated or unsaturated, hydrocarbon chain, having from 1 to 20 carbon atoms, wherein one or more of the carbon atoms is optionally replaced by (—O—) or (—NR—), and wherein the chain is optionally substituted on carbon with one or more oxo substituents.

10. The implantable device of claim 6 wherein L is a divalent, branched or unbranched, saturated or unsaturated, hydrocarbon chain, having from 3 to 15 carbon atoms, wherein one or more of the carbon atoms is optionally replaced by (—O—) or (—NR—), and wherein the chain is optionally substituted on carbon with one or more substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy.

11. The implantable device of claim 6 wherein L is a divalent, branched or unbranched, saturated or unsaturated, hydrocarbon chain, having from 3 to 15 carbon atoms, wherein one or more of the carbon atoms is optionally replaced by (—O—) or (—NR—), and wherein the chain is optionally substituted on carbon with one or more oxo substituents.

12. The implantable device of claim 6 wherein L is a divalent, branched or unbranched, saturated or unsaturated, hydrocarbon chain, having from 3 to 15 carbon atoms, wherein the chain is optionally substituted on carbon with one or more oxo substituents.

13. The implantable device of claim 6 wherein L is a divalent, branched or unbranched, hydrocarbon chain, having from 4 to 8 carbon atoms, wherein the chain is optionally substituted on carbon with one or more oxo substituents.

14. The implantable device of claim 13 wherein L is —CH$_2$CH$_2$CH$_2$CH$_2$—.

15. The implantable device of claim 6 wherein L is —C(=O)(CH$_2$)$_n$C(=O)—; wherein n is 1, 2, 3, 4, 5, 6, 7, 8, 9, or 10.

16. An iodinated polyanhydride as described in claim 1.

17. The implantable device of claim 8 wherein L is a divalent, branched or unbranched, saturated or unsaturated, hydrocarbon chain, having from 1 to 20 carbon atoms, wherein one or more of the carbon atoms is optionally replaced by (—O—) or (—NR—), and wherein the chain is optionally substituted on carbon with one or more oxo substituents.

18. The implantable device of claim 8 wherein L is a divalent, branched or unbranched, saturated or unsaturated, hydrocarbon chain, having from 3 to 15 carbon atoms, wherein one or more of the carbon atoms is optionally replaced by (—O—) or (—NR—), and wherein the chain is optionally substituted on carbon with one or more substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy.

19. The implantable device of claim 8 wherein L is a divalent, branched or unbranched, saturated or unsaturated, hydrocarbon chain, having from 3 to 15 carbon atoms, wherein one or more of the carbon atoms is optionally replaced by (—O—) or (—NR—), and wherein the chain is optionally substituted on carbon with one or more oxo substituents.

20. The implantable device of claim 8 wherein L is a divalent, branched or unbranched, saturated or unsaturated, hydrocarbon chain, having from 3 to 15 carbon atoms, wherein the chain is optionally substituted on carbon with one or more oxo substituents.

21. The implantable device of claim 8 wherein L is a divalent, branched or unbranched, hydrocarbon chain, having from 4 to 8 carbon atoms, wherein the chain is optionally substituted on carbon with one or more oxo substituents.

22. The implantable device of claim 21 wherein L is —$CH_2CH_2CH_2CH_2$—.

23. The implantable device of claim 8 wherein L is —$C(=O)(CH_2)_nC(=O)$—; wherein n is 1, 2, 3, 4, 5, 6, 7, 8, 9, or 10.

* * * * *

UNITED STATES PATENT AND TRADEMARK OFFICE
CERTIFICATE OF CORRECTION

PATENT NO. : 8,361,453 B2
APPLICATION NO. : 12/303682
DATED : January 29, 2013
INVENTOR(S) : Uhrich et al.

Page 1 of 1

It is certified that error appears in the above-identified patent and that said Letters Patent is hereby corrected as shown below:

In he Claims:

In Column 34 Line 11,

Please replace the final figure in the sequence with:

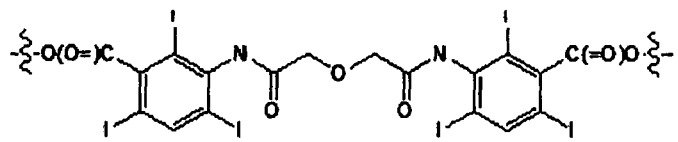

Signed and Sealed this
Thirtieth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,361,453 B2  Page 1 of 1
APPLICATION NO. : 12/303682
DATED : January 29, 2013
INVENTOR(S) : Uhrich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1057 days.

Signed and Sealed this
First Day of September, 2015

Michelle K. Lee
*Director of the United States Patent and Trademark Office*